(12) United States Patent
Manabe et al.

(10) Patent No.: US 10,940,056 B2
(45) Date of Patent: Mar. 9, 2021

(54) ABSORBENT ARTICLE AND METHOD OF MANUFACTURING SAME

(71) Applicant: Daio Paper Corporation, Ehime (JP)

(72) Inventors: Sadanao Manabe, Tokyo (JP); Akifumi Hayashi, Tokyo (JP)

(73) Assignee: Daio Paper Corporation, Ehime (JP)

( * ) Notice: Subject to any disclaimer, the term of this patent is extended or adjusted under 35 U.S.C. 154(b) by 335 days.

(21) Appl. No.: 15/761,470

(22) PCT Filed: Aug. 4, 2016

(86) PCT No.: PCT/JP2016/072989
§ 371 (c)(1),
(2) Date: Mar. 20, 2018

(87) PCT Pub. No.: WO2017/056715
PCT Pub. Date: Apr. 6, 2017

(65) Prior Publication Data
US 2018/0256416 A1    Sep. 13, 2018

(30) Foreign Application Priority Data
Sep. 30, 2015 (JP) .............................. JP2015-194544

(51) Int. Cl.
*A61F 13/539* (2006.01)
*A61F 13/15* (2006.01)
(Continued)

(52) U.S. Cl.
CPC ...... *A61F 13/539* (2013.01); *A61F 13/15617* (2013.01); *A61F 13/15658* (2013.01);
(Continued)

(58) Field of Classification Search
CPC ...... A61F 2013/5315; A61F 2013/5349; A61F 2013/530481–530496;
(Continued)

(56) References Cited

U.S. PATENT DOCUMENTS 6,573,422 B1 * 6/2003 Rosenfeld ........... A61F 13/4756
604/368
2009/0076473 A1   3/2009 Kasai et al.
(Continued)

FOREIGN PATENT DOCUMENTS

CN        1263760      12/2004
CN       101888822     11/2010
(Continued)

OTHER PUBLICATIONS

Office Action for CN201680053201, dated Mar. 27, 2020.
International Search Report for PCT/JP2016/072989 dated Nov. 1, 2016.

*Primary Examiner* — Susan S Su
(74) *Attorney, Agent, or Firm* — Andrus Intellectual Property Law, LLP

(57) ABSTRACT

An absorbent article has an absorbent body obtained by mixing and accumulating fibers and high absorbent polymer particles. A wrapping sheet includes an intermediate part located on a front face side of the absorbent body and both side parts folded back to a back face side of the absorbent body from the intermediate part. Distal ends of the both side parts of the wrapping sheet are overlapped on the back face side of the absorbent body to form a connecting portion. A total weight of the high absorbent polymer particles is larger than a total weight of the fibers in the absorbent body. A content rate of the high absorbent polymer particles of the absorbent body increases stepwise or continuously from the back face side toward the front face side.

7 Claims, 19 Drawing Sheets

(51) Int. Cl.
*A61F 13/535* (2006.01)
*A61F 13/532* (2006.01)
*A61F 13/537* (2006.01)
*A61F 13/53* (2006.01)

(52) U.S. Cl.
CPC .. *A61F 13/15666* (2013.01); *A61F 13/15682* (2013.01); *A61F 13/15739* (2013.01); *A61F 13/15747* (2013.01); *A61F 13/535* (2013.01); *A61F 13/5323* (2013.01); *A61F 13/53713* (2013.01); *A61F 2013/15349* (2013.01); *A61F 2013/53051* (2013.01); *A61F 2013/530481* (2013.01); *A61F 2013/530868* (2013.01); *A61F 2013/53908* (2013.01)

(58) Field of Classification Search
CPC ........ A61F 2013/530532; A61F 2013/530576; A61F 2013/5307
USPC .................................. 604/358–392
See application file for complete search history.

(56) References Cited

U.S. PATENT DOCUMENTS

| | | | |
|---|---|---|---|
| 2010/0312206 A1 | 12/2010 | Fujioka | |
| 2011/0313384 A1* | 12/2011 | Akiyama | A61F 13/53717 604/378 |
| 2012/0296294 A1 | 11/2012 | Hashimoto et al. | |
| 2012/0302985 A1* | 11/2012 | Mukai | A61F 13/15723 604/385.24 |
| 2014/0276518 A1* | 9/2014 | Varona | A61F 13/58 604/372 |
| 2016/0175169 A1* | 6/2016 | Bianchi | A61F 13/15699 604/372 |
| 2017/0095380 A1* | 4/2017 | Wirtz | A61F 13/534 |

FOREIGN PATENT DOCUMENTS

| | | |
|---|---|---|
| CN | 101151010 A | 6/2012 |
| EP | 0 600 454 | 6/1994 |
| EP | 1 023 884 | 8/2000 |
| EP | 1870067 A | 12/2007 |
| JP | 2002-165834 | 6/2002 |
| JP | 2006305327 A | 11/2006 |
| JP | 200737668 A | 2/2007 |
| JP | 2007-144101 | 6/2007 |
| JP | 2013252332 A | 12/2013 |
| JP | 2013252333 A | 12/2013 |
| JP | 2014110890 A | 6/2014 |
| JP | 2015-66027 | 4/2015 |
| JP | 201566382 A | 4/2015 |
| JP | 2015-119922 | 7/2015 |
| WO | 2006109524 A1 | 10/2006 |
| WO | 2015046516 A1 | 4/2015 |

* cited by examiner (a)

(b)

ABSORBENT ARTICLE AND METHOD OF MANUFACTURING SAME

CROSS-REFERENCE TO RELATED APPLICATIONS

This application is the U.S. national stage application of International Application PCT/JP2016/072989, filed Aug. 4, 2016, which international application was published on Apr. 6, 2017, as International Publication WO 2017/056715. The International Application claims priority of Japanese Patent Application No. 2015-194544, filed Sep. 30, 2015. The international application and Japanese application are both incorporated herein by reference, in entirety.

TECHNICAL FIELD

The present invention relates to an absorbent article characterized by a wrapping technology for an absorbent body and a method of manufacturing the same.

BACKGROUND ART

In an absorbent article such as a disposable diaper, a sanitary napkin, etc., a mixture of fibers such as pulp fibers and high absorbent polymer particles is generally used as an absorbent body. Further, in general, such an absorbent body is incorporated as an absorbent element formed by being wound by a wrapping sheet made of a crepe tissue, etc. to increase shape maintainability during manufacture and after manufacture.

FIG. 17 to FIG. 19 illustrate a manufacturing facility/process example of a conventional absorbent element. In this manufacturing facility 100, first, a mixture of pulp fibers obtained by defibrating a pulp sheet 56F using a defibrating machine 101 and high absorbent polymer particles 56P is supplied from above a fiber accumulating drum 102 which is laterally disposed and rotationally driven. Absorbent body molds 102m each of which has a rotation direction corresponding to a front-back direction is formed in a concave shape on an outer peripheral surface of the fiber accumulating drum 102, a plurality of suction holes is formed in a bottom face of each absorbent body mold 102m, and the mixture of the pulp fibers and the high absorbent polymer particles 56P is accumulated in the absorbent body mold 102m by suction from the suction holes in the absorbent body mold 102m to form an absorbent body 56 at a feed location of the pulp fibers and the high absorbent polymer particles 56P. When the absorbent body 56 formed in the absorbent body mold 102m is at a location facing a continuum-shaped wrapping sheet 58 supplied along the outer peripheral surface of the fiber accumulating drum 102 by rotation of the fiber accumulating drum 102, the absorbent body 56 leaves the mold and is transferred (moved) onto the wrapping sheet 58. A first adhesive layer G1 is formed on a surface of the wrapping sheet 58 onto which the absorbent body 56 is transferred by applying of a hot melt adhesive M1 in advance, and the absorbent body 56 is bonded to the wrapping sheet 58 by the first adhesive layer G1. The absorbent body 56 is intermittently supplied onto the continuously conveyed wrapping sheet 58 by successively performing these processes.

The absorbent body 56 transferred onto the wrapping sheet 58 is tightly compressed over a maximum width of the absorbent body 56 by a belt conveyor-type pressing device 103 which faces the absorbent body 56 before the wrapping sheet 58 is wound around the absorbent body 56.

A width of the wrapping sheet 58 in a cross direction (CD) orthogonal to a machine direction (MD) (a conveying direction of the sheet) is wider than that of the absorbent body 56. After the absorbent body 56 is transferred onto an intermediate part 58c in the CD of the wrapping sheet and compressed by the pressing device 103, a second adhesive layer G2 is formed over a maximum width of an upper surface of the absorbent body 56 by applying a hot melt adhesive M2. Further, thereafter, both side parts 58s of the wrapping sheet extending beyond both sides of the absorbent body 56 in the CD are folded back at positions along both side edges of the absorbent body 56 and bonded to the upper surface of the absorbent body 56 by a sailor (not illustrated), and both end portions in the CD of the wrapping sheet are overlapped and bonded each other by a third adhesive layer G3 formed by applying a hot melt adhesive M3 to an overlapping portion in advance, thereby forming a connecting portion 58c.

In this way, a continuous body of an absorbent element 50 to which the absorbent body 56 is intermittently fixed in the MD is formed in a barrel-shaped continuous body of the wrapping sheet 58 which is continuous in the MD. The continuous body of the absorbent element 50 becomes an individual absorbent element 50 by being intermittently cut in the MD in a state in the middle of manufacturing in which another member is attached, in a state in which another member is not attached, or in a cutting process of obtaining an individual finished product.

Meanwhile, various absorption performances are required from the absorbent article, and returning is typical for the absorption performances. Returning refers to a phenomenon in which urine once absorbed by the absorbent body returns to a surface of the article again. When the returning is likely to occur, there is a problem a skin is unnecessarily contaminated by excretion. Thus, an article that rarely causes the returning is desired.

CITATION LIST

Patent Literature

Patent Literature 1: JP 2007-144101 A
Patent Literature 2: JP 2002-165834 A
Patent Literature 3: JP 2015-066027 A The inventors have conducted research on a scheme of improved prevention of returning known as a phenomenon in which liquid content of excretion entering the absorbent body side returns to the skin side by increasing a content rate of high absorbent polymer particles in the absorbent body and increasing a content rate of high absorbent polymer particles on a surface of the absorbent body, and has found the following problems in this process.

In more detail, in a case in which the absorbent element manufactured by the above-described manufacturing method is incorporated in the absorbent article without changing a direction, after accumulation is performed such that a large amount of the high absorbent polymer particles is contained on a bottom side of each absorbent body mold in the fiber accumulating drum and the absorbent body is transferred onto the wrapping sheet (in this instance, upper and lower sides of the absorbent body are switched), the both side parts of the wrapping sheet in the width direction are folded back on the absorbent body, and distal ends thereof are overlapped and bonded to each other to form the connecting portion. In this case, a part of the absorbent body in which the content rate of the high absorbent polymer particles is high is located under the connecting portion side of the wrapping sheet. Thus, when bonding of the connecting portion of the wrapping sheet is insufficient, there is concern that high absorbent polymer particles leaving the absorbent body may leak out from the connecting portion of the wrapping sheet to a skin side of a wearer.

In addition, when accumulation is performed such that a large amount of the high absorbent polymer particles is contained on the bottom side of each absorbent body mold in the fiber accumulating drum, there is a problem that the high absorbent polymer particles are likely to be clogged in the suction holes of the absorbent body mold.

In this regard, a main object of the invention is to reduce a risk of leakage of high absorbent polymer particles from the connecting portion of the wrapping sheet while preventing the returning.

Solution to Problem

The invention solving the above-mentioned problem is as follows.

<Invention Described in Claim 1>

An absorbent article, comprising an absorbent element obtained by wrapping an absorbent body in a wrapping sheet, wherein the absorbent body is obtained by mixing and accumulating fibers and high absorbent polymer particles, the wrapping sheet includes an intermediate part located on a front face side of the absorbent body and both side parts folded back to a back face side of the absorbent body from the intermediate part, and distal ends of the both side parts of the wrapping sheet are overlapped on the back face side of the absorbent body to form a connecting portion, a total weight of the high absorbent polymer particles is larger than a total weight of the fibers in the absorbent body, and a content rate of the high absorbent polymer particles of the absorbent body increases stepwise or continuously from the back face side toward the front face side.

(Effects)

In the invention, the content rate of the high absorbent polymer particles of the absorbent body is high, and the content rate increases stepwise or continuously from the back face side toward the front face side. Thus, returning preventing property is excellent. Nevertheless, since the connecting portion of the wrapping sheet is located under the back face side of the absorbent body (that is, an opposite side from a part of the absorbent body in which the content rate of the high absorbent polymer particles is high), even when bonding of the connecting portion of the wrapping sheet is insufficient, the high absorbent polymer particles rarely leak out. In addition, even when high absorbent polymer particles leaving the absorbent body leak out from the connecting portion of the wrapping sheet, this happens under the back face side of the absorbent element, and thus concern about leakage to the skin side of the wearer is small. Further, an overlapping part of the wrapping sheet has higher liquid retentivity than that of another part. Thus, when the overlapping part is located on the front face side of the absorbent body, there is concern that the returning may be promoted. However, since the overlapping part is located under the back face side of the absorbent body in the invention, such a problem does not occur.

<Invention Described in Claim 2>

The absorbent article according to claim 1, wherein a whole part of an internal surface of the wrapping sheet facing the absorbent body is bonded to an external surface of the absorbent body through a hot melt adhesive, and a usage amount of the hot melt adhesive bonding the wrapping sheet and the absorbent body together is larger at least in a region of both end portions in a width direction on the back face side of the absorbent body than on the front face side of the absorbent body.

(Effects)

The inventors have found that a cause of promoting easiness of shape deformation of the absorbent body is hidden in a manufacturing process of a wrapping sheet winding type absorbent element in a development process of a manufacturing facility. That is, in the wrapping sheet winding type absorbent element, during manufacture, after bonding the lower surface of the absorbent body and the intermediate portion of the wrapping sheet together at the time of transferring the absorbent body, the both side parts of the wrapping sheet are folded back and bonded to the upper surface of the absorbent body. Thus, both the front face side and back face side of the absorbent body may not be bonded under the same condition. Here, to fold back and bond both the side parts of the wrapping sheet to the upper surface of the absorbent body, when the hot melt adhesive is applied to the upper surface of the absorbent body in advance, and the both side parts of the wrapping sheet are folded back and bonded thereto, there is an advantage that an upper surface shape of the absorbent body is stable. Thus, such a scheme has been adopted. However, the surface of the absorbent body has low density and large unevenness even when the surface is compressed using a pressing device. For this reason, in a case in which the hot melt adhesive is applied to the absorbent body and bonded to the wrapping sheet, bonding is relatively weak when compared to a case of applying the hot melt adhesive to the wrapping sheet and bonding the wrapping sheet to the absorbent body at the same usage amount of the hot melt adhesive (refers to a weight per unit area, which is applied to description below). That is, an application scheme adopted to ensure stability of the shape of the upper surface of the absorbent body in folding back the wrapping sheet has caused risk of causing shape deformation of the absorbent body in a product.

In particular, the hot melt adhesive bonded to the absorbent body may cause absorption inhibition in some cases, and it is desired that the usage amount thereof is the minimum necessary. Therefore, when an unintentional decrease in adhesive force as described above occurs, the shape maintenance action by the wrapping sheet tends to deteriorate.

The invention has been conceived by obtaining such knowledge. Further, when the whole part of the internal surface of the wrapping sheet facing the absorbent body is bonded to the external surface of the absorbent body through the hot melt adhesive, and the usage amount of the hot melt adhesive for bonding the absorbent body and the wrapping sheet together at least in the region of the both end portions in the width direction is increased on the back face side of the absorbent body where the adhesive force is likely to decrease (the side of the absorbent body having the wrapping sheet connecting portion) rather than on the front face side of the absorbent body, it is possible to effectively suppress shape deformation of the absorbent body while suppressing a total usage amount of the hot melt adhesive for bonding the absorbent body and the wrapping sheet together.

In addition, in such a wrapping sheet winding mode, when the both side parts of the wrapping sheet are folded back and bonded, high absorbent polymer particles pushed out at the both sides of the absorbent body may be brought out with the wrapping sheet, and thus the number of high absorbent polymer particles may increase at the both sides of the absorbent body on the face side having the wrapping sheet connecting portion. In the invention, the high absorbent polymer particles at the both sides of the absorbent body on the face having the wrapping sheet connecting portion side may be also bonded to prevent a decrease in strength of the absorbent body.

<Invention Described in Claim 3>

The absorbent article according to claim 2, wherein two narrowing portions are formed by narrowing both sides of the absorbent body toward a center side in the width direction at an intermediate portion in a front-back direction of the absorbent body and a region in which the usage amount of the hot melt adhesive bonding the wrapping sheet and the absorbent body together is larger than the usage amount on the front face side of the absorbent body corresponds to a region including the whole narrowing portions in the width direction.

(Effects)

When the narrowing portions for improving the fitting property around the legs are formed in the absorbent body, it is possible to suppress shape deformation of the absorbent body at the narrowing portions by setting a region, in which the large amount of the hot melt adhesive is used for bonding the wrapping sheet and the absorbent body together, to a region including the whole narrowing portions in the width direction as described in this claim. In a disposable diaper, it is usual that narrowing portions are formed in the absorbent body. Then, since a part interposed between both legs is the most stressful part, it is possible to particularly effectively suppress deformation of the absorbent body by adopting a configuration described in this claim. In addition, the hot melt adhesive may effectively capture and fix high absorbent polymer particles spilled out to the narrowing portions from the absorbent body.

<Invention Described in Claim 4>

The absorbent article according to claim 2 or 3, wherein a slit penetrating the absorbent body in a thickness direction extends in the front-back direction at an intermediate portion of the absorbent body in the width direction, and the region in which the usage amount of the hot melt adhesive bonding the wrapping sheet and the absorbent body together is larger than the usage amount on the front face side of the absorbent body corresponds to a region including both end portions of the slit in the width direction.

(Effects)

When the slit penetrating the absorbent body in the thickness direction is formed in the absorbent body to improve liquid diffusibility in the front-back direction, shape deformation of the absorbent body in the slit may be suppressed by setting the region in which, the usage amount of the hot melt adhesive bonding the wrapping sheet and the absorbent body together is large, to the region including the both end portions of the slit in the width direction as described in this claim. In addition, the hot melt adhesive may effectively capture and fix high absorbent polymer particles spilled out to the slit portion from the absorbent body.

<Invention Described in Claim 5>

The absorbent article according to any one of claims 2 to 4, wherein the region in which the usage amount of the hot melt adhesive bonding the wrapping sheet and the absorbent body together is larger than the usage amount on the front face side of the absorbent body corresponds to a region in which the number of stacked hot melt adhesive layers is larger than the number on the one side of the absorbent body.

(Effects)

To increase the usage amount of the hot melt adhesive locally, the amount can be increased locally in each application. However, since such a treatment is often difficult, it is preferable to increase the usage amount based on the number of stacked layers as described in this claim.

<Invention Described in Claim 6>

The absorbent article according to any one of claims 2 to 5, wherein a plurality of hot melt adhesive layers among which at least one of an application pattern and a type of the hot melt adhesive is different is stacked in the region in which the usage amount of the hot melt adhesive bonding the wrapping sheet and the absorbent body together is larger than the usage amount on the front face side of the absorbent body, and a layer of the hot melt adhesive, on the front face side of the absorbent body, bonding the wrapping sheet and the absorbent body together has the same application pattern and type as an application pattern and type of a layer located closest to the wrapping sheet among the plurality of hot melt adhesive layers.

<Invention Described in Claim 7>

A method of manufacturing an absorbent article using an absorbent element, comprising forming an absorbent body by accumulating a mixture of fibers and high absorbent polymer particles in at least one absorbent body mold while performing suction from a plurality of suction holes with a laterally disposed and rotationally driven fiber accumulating drum provided with, on an outer peripheral surface thereof, the absorbent body mold having a concave shape, a rotation direction corresponding to a front-back direction, and in a bottom face thereof, the plurality of suction holes, transferring the absorbent body formed in the absorbent body mold to an intermediate part in a width direction on an upper surface of a wrapping sheet, folding back parts of the wrapping sheet located at both sides of the absorbent body in the width direction to an upper side of the absorbent body, respectively, overlapping distal ends of folded portions to form a connecting portion, and bonding an internal surface of the wrapping sheet and an external surface of the absorbent body through a hot melt adhesive, thereby manufacturing the absorbent element obtained by wrapping the absorbent body in the wrapping sheet, wherein a total weight of the high absorbent polymer particles is larger than a total weight of the fibers in the absorbent body, the accumulating is performed such that a content rate of the high absorbent polymer particles of the absorbent body formed in the absorbent body mold increases stepwise or continuously from a bottom side toward an inlet side of the absorbent body mold, and the connecting portion of the wrapping sheet is incorporated in the absorbent article such that the connecting portion corresponds to a back face side of the absorbent body in the absorbent article.

(Effects)

According to the manufacturing method described in this claim, it is possible to manufacture the absorbent article having the above-described advantage. In addition, in the manufacturing method described in this claim, accumulation is performed such that a large amount of the high absorbent polymer particles is contained on the inlet side of the absorbent body mold in the fiber accumulating drum, and thus a problem that the high absorbent polymer particles are likely to be clogged in the suction holes of the absorbent body mold rarely occurs.

<Invention Described in Claim 8>

The method of manufacturing an absorbent article according to claim 7, wherein after the absorbent body is transferred to the intermediate part in the width direction on the upper surface of the wrapping sheet, and before folding back the parts of the wrapping sheet located at the both sides of the absorbent body in the width direction to the upper side of the absorbent body, respectively, a hot melt adhesive is applied to the upper surface of the absorbent body.

(Effects)

In the case in which the both side parts of the wrapping sheet are folded back and bonded to the upper surface of the absorbent body, when the hot melt adhesive is applied to the upper surface of the absorbent body in advance, and the both side parts of the wrapping sheet are folded back and bonded thereto, there is an advantage that an upper surface shape of the absorbent body is stable. Here, when accumulation is performed such that a large amount of the high absorbent polymer particles is contained on the bottom side of the absorbent body mold in the fiber accumulating drum, and the high absorbent polymer particles are transferred onto the wrapping sheet (in this instance, upper and lower sides of the absorbent body are switched) as in the past, a large amount of the high absorbent polymer particles is contained on the upper surface side of the absorbent body. Thus, there is a problem that when the hot melt adhesive is applied to the upper surface of the absorbent body, the high absorbent polymer particles are likely to scatter due to an application force thereof. On the other hand, in the invention, accumulation is performed such that the content rate of the high absorbent polymer particles increases stepwise and continuously from the bottom side toward the inlet side of the absorbent body mold in the fiber accumulating drum. Thus, when the hot melt adhesive is applied to the upper surface of the absorbent body, the content rate of the high absorbent polymer particles decreases toward the upper surface side of the absorbent body, and the high absorbent polymer particles rarely scatter.

<Invention Described in Claim 9>

The method of manufacturing an absorbent article according to claim 7 or 8, wherein after the manufactured absorbent element is reversed upside down, a member to be mounted on a front face side of the absorbent body in the absorbent article is attached to an upper side of the absorbent element, and a member to be mounted on the back face side of the absorbent body in the absorbent article is attached to a lower side of the absorbent element.

(Effects)

In this way, when after the absorbent element is manufactured without changing the orientation immediately after the fiber accumulating drum, the orientation of the absorbent element is reversed upside down, and the member is attached to both upper and lower sides, application to existing design is easy, and thus it is preferable.

Advantageous Effects of Invention

As described above, the invention has an advantage of being able to reduce a risk of leakage of high absorbent polymer particles from the connecting portion of the wrapping sheet while preventing returning.

DESCRIPTION OF EMBODIMENTS

Figure 1:
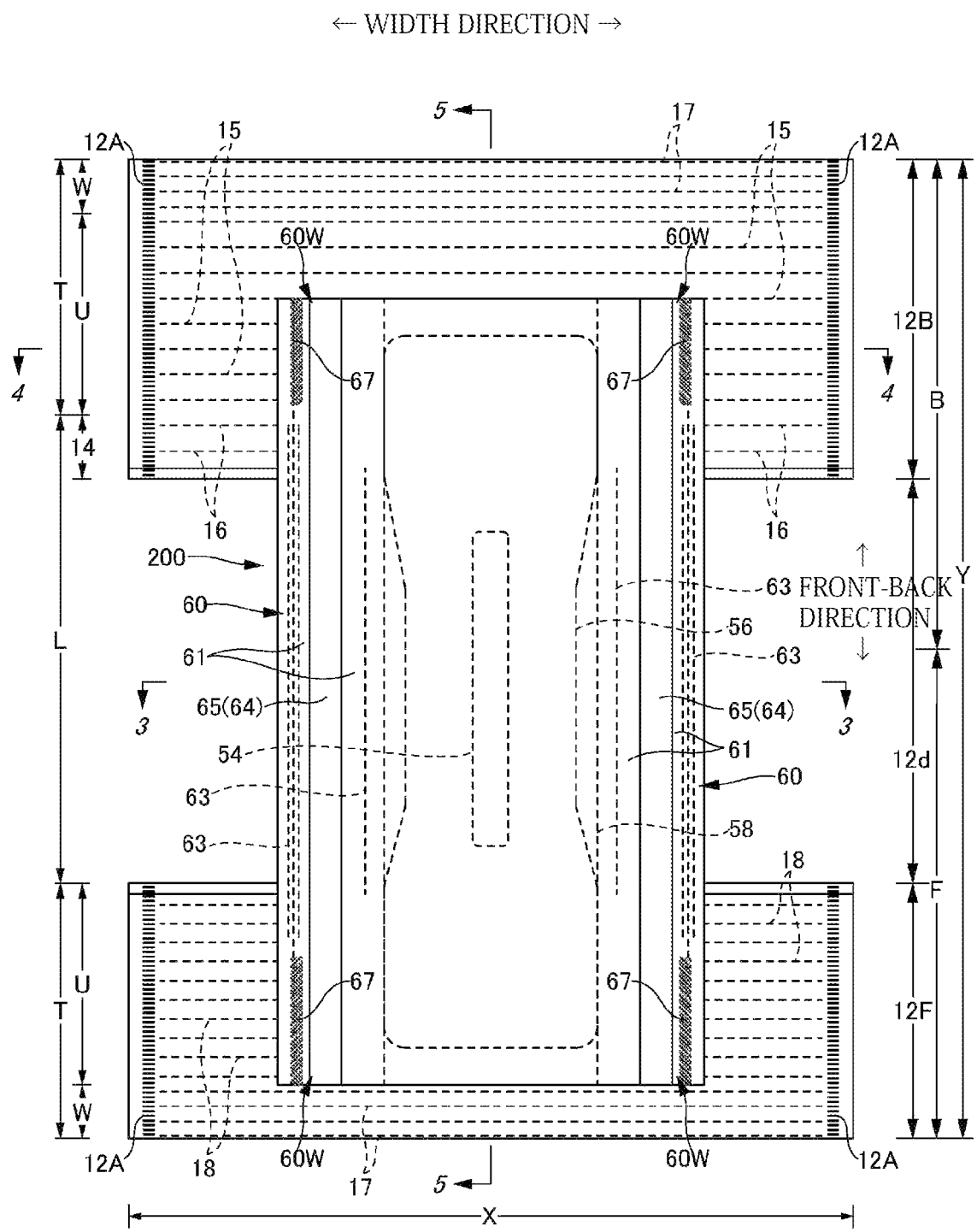
FIG. 1 is a plan view of a spread state illustrating an internal surface of an underpants-type disposable diaper.
Figure 2:
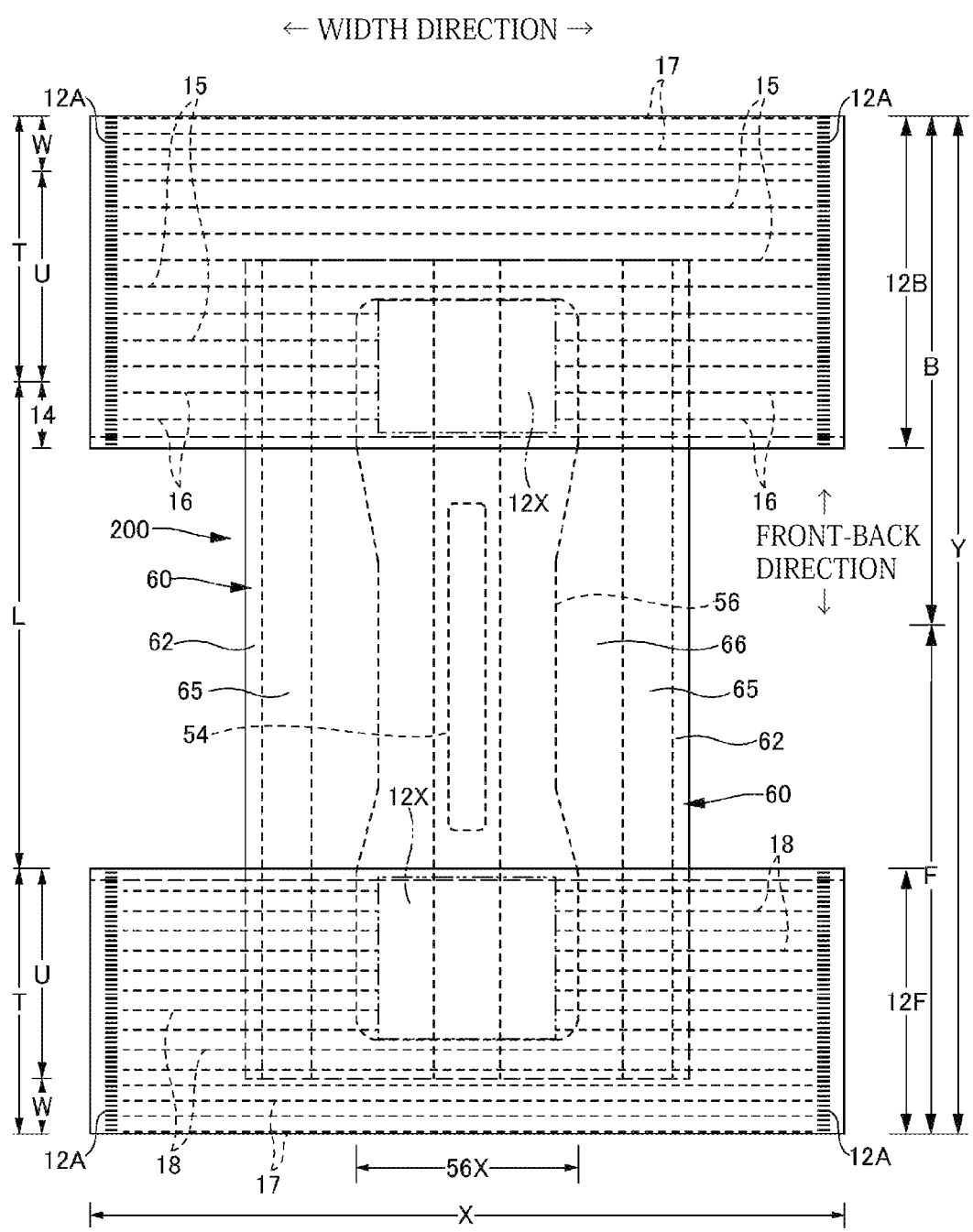
FIG. 2 is a plan view of a spread state illustrating an external surface of the underpants-type disposable diaper.

Hereinafter, an embodiment of the invention will be described in detail with reference to accompanying drawings.

FIG. 1 to FIG. 6 illustrate an example of an underpants-type disposable diaper. A dotted portion in a cross-sectional view indicates an adhesive serving as joining means that joins respective constituent members located on a front face side and a back face side, and is formed by solid, bead, curtain, summit or spiral coating, etc. of a hot melt adhesive, etc. or by application of the adhesive to an outer peripheral surface of an elastically stretchable member with a comb gun or Surewrap nozzle, etc. in place of or together with the above-mentioned coating in a fixed portion of the elastically stretchable member. It is possible to use fixing means based on material welding such as heat sealing, ultrasonic sealing, etc. as the joining means that joins the respective constituent members.

The underpants-type disposable diaper of the present mode includes an outer member including a single segment or two discrete segments 12F and 12B and disposed in a front body F and a back body B and an inner member 200 fixed to the inner face of the outer member 12F and 12B from the front body F to the back body B through a crotch portion, and both side portions of the outer member 12F of the front body F and both side portions of the outer member 12B of the back body B are joined to form side seal portions 12A. Reference symbol Y indicates a whole length (a longitudinal direction from an edge of a waist opening WO of the front body F to an edge of a waist opening WO of the back body B) of the diaper in a spread state, and reference symbol X indicates a maximum width of the diaper in the spread state.

The inner member 200 is a portion that absorbs and holds excretion such as urine, and the outer member 12 is a portion for supporting the inner member 200 with respect to a body of a wearer. In the present mode, an upper opening of the outer members 12F and 12B corresponds to the waist opening WO through which the trunk of a wearer passes, and a portion surrounded by each of lower edges of the outer members 12F and 12B and side edges of the inner member 200 at both sides of the inner member 200 in the width direction corresponds to a leg opening LO through which the leg passes.

In addition, the underpants-type disposable diaper of the present mode includes a lower torso region T defined as a longitudinal range having the side seal portions 12A (a longitudinal range from the waist opening WO to an upper end of the leg opening LO) and an intermediate region L defined as a front-back direction range of a portion forming the leg opening LO (between a longitudinal region having the side seal portions 12A of the front body F and a longitudinal region having the side seal portions 12A of the back body B). The lower torso region T may be conceptually divided into a "waist portion" W forming an edge portion of the waist opening and an "under-waist portion" U corresponding to a portion below the "waist portion" W. Normally, in a case of having a boundary at which stretching stress in the width direction changes (for example, a fineness or a stretch rate of the elastically stretchable member changes) in the lower torso region T, the waist opening WO side with respect to the boundary closest to the waist opening WO corresponds to the waist portion W. In a case of not having such a boundary, the waist opening WO side with respect to the absorbent body 56 or the inner member 200 corresponds to the waist portion W. Longitudinal lengths thereof are different according to a size of a product and may be appropriately determined. However, as an example, the waist portion W may be set to 15 to 40 mm, and the under-waist portion U may be set to 65 to 120 mm Meanwhile, both side edges of the intermediate region L are narrowed in a U shape or a curved shape to conform to the leg of the wearer, and this portion corresponds to a part into which the leg of the wearer is put. As a result, the underpants-type disposable diaper in the spread state from which the side seal portions 12A are peeled off substantially has an hourglass shape as a whole.

(Outer Member)

Figure 9:
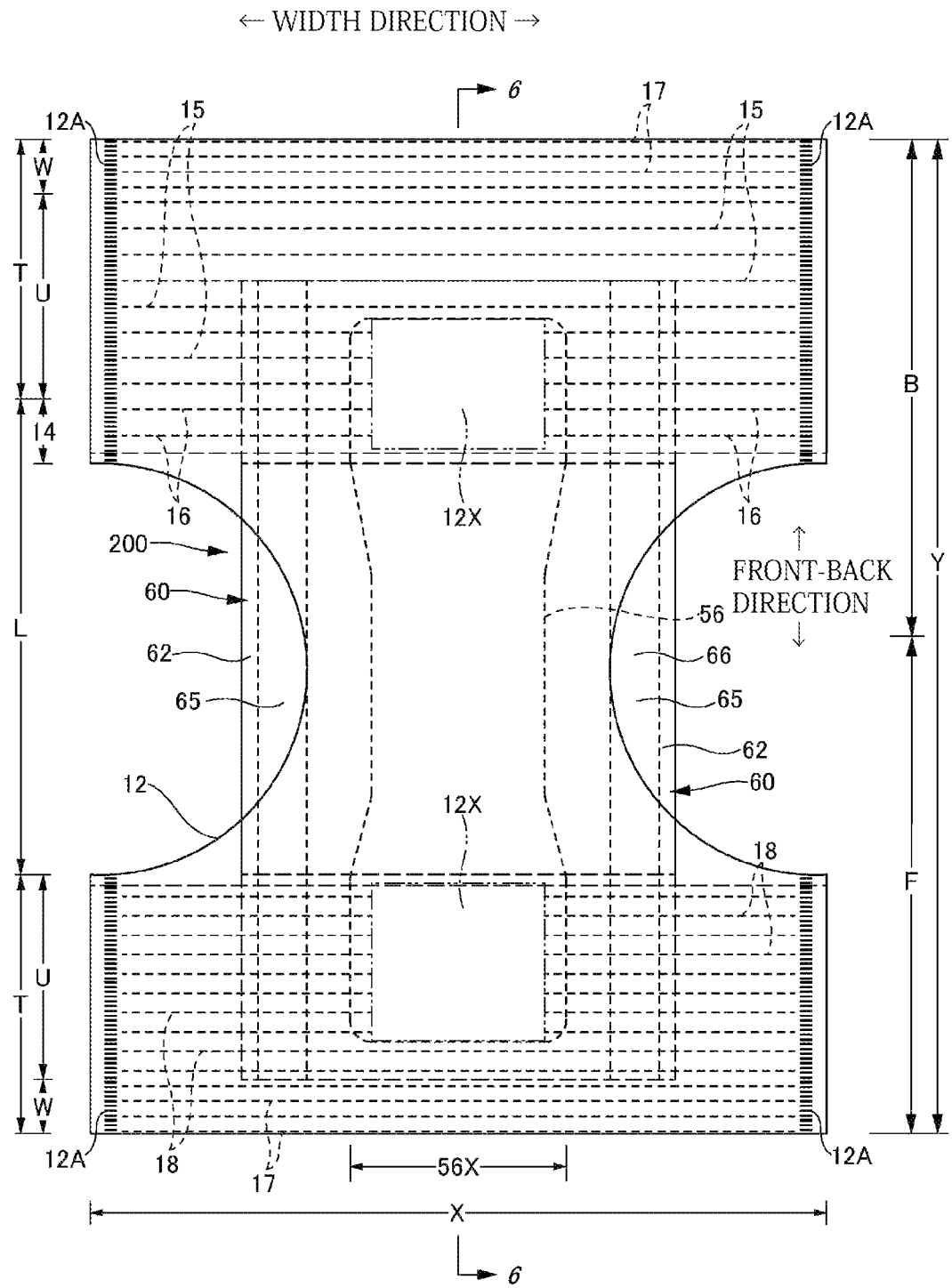
FIG. 9 is a plan view of a spread state illustrating an external surface of an underpants-type disposable diaper.
Figure 10:
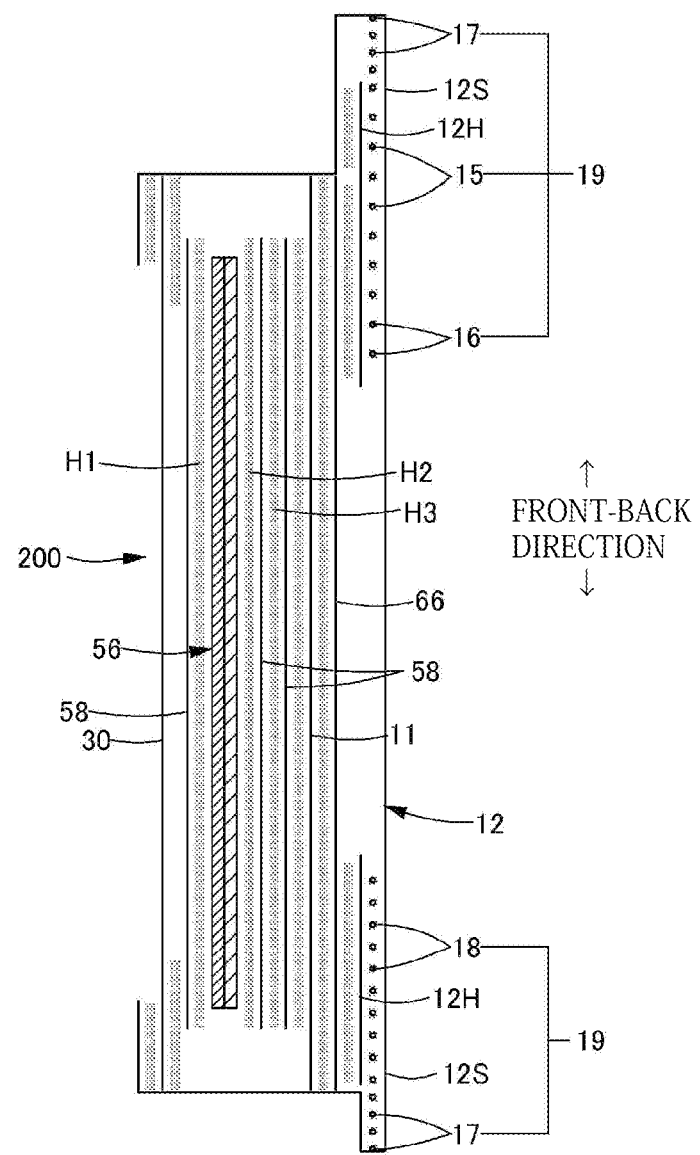
FIG. 10 is a cross-sectional view illustrating a layer configuration of 6-6 cross section of FIG. 9.

The outer members 12F and 12B, respectively, function as a front outer member 12F in the front body F and a back outer member 12B in the back body B. The front outer member 12F and the back outer member 12B are discontinuous or separated from each other in the regions adjacent to the legs. A clearance 12d may be set to about 150 to 250 mm. Although not illustrated, it is possible to paste a crotch portion cover sheet made of a nonwoven fabric, etc. to cover a part (for example, over a whole of a portion in the front-back direction exposed between the front side outer member 12F and the back side outer member 12B and not extending up to front and back ends of the inner member 200, and a degree at which both side edges in the width direction does not reach up to the both side edges of the inner member 200) or a whole of an exposed portion of a back surface of the inner member 200 in this separated portion. In addition, as illustrated in FIG. 9 and FIG. 10, the outer member 12 may be integrally formed to continue through the crotch from the front body F to the back body B. That is, the outer members 12F and 12B in the front body F and the back body B, respectively, are separated as two discrete segments in the former configuration, whereas the outer members 12 in the front body F and back body B are unified as the single segment in the latter configuration.

The outer members 12F and 12B have a lower torso portion which corresponds to a longitudinal range corresponding to the lower torso region T. In addition, in the present mode, the front side outer member 12F has a part corresponding to the intermediate region L. However, the back side outer member 12B has a gluteal region cover portion 14 extending from the lower torso region T to the intermediate region L side. Although not illustrated, an inguinal cover portion extending from the lower torso region T to the intermediate region L side may be provided in the front side outer member 12F, it is possible to adopt a mode in which the inguinal cover portion is provided and the gluteal region cover portion is not provided, or a part corresponding to the intermediate region L may not be provided in both the front side outer member 12F and the back side outer member 12B. In addition, in the illustrated mode, a lower edge of the gluteal region cover portion 14 is formed in a linear shape along the width direction similarly to the lower edge of the front side outer member 12F. However, the lower edge may be set to a curve located on the waist opening side toward an outer side in the width direction.

Figure 3:
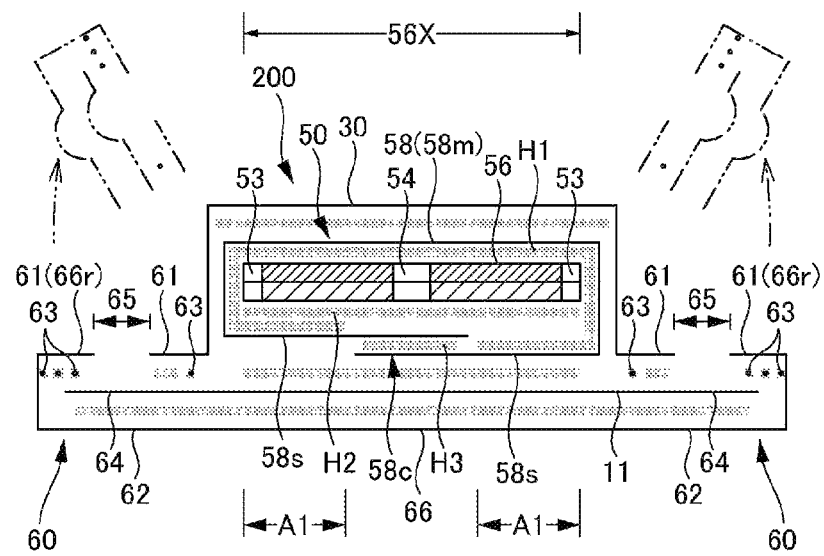
FIG. 3 is a cross-sectional view illustrating a layer configuration of 3-3 cross section of FIG. 1.
Figure 4:
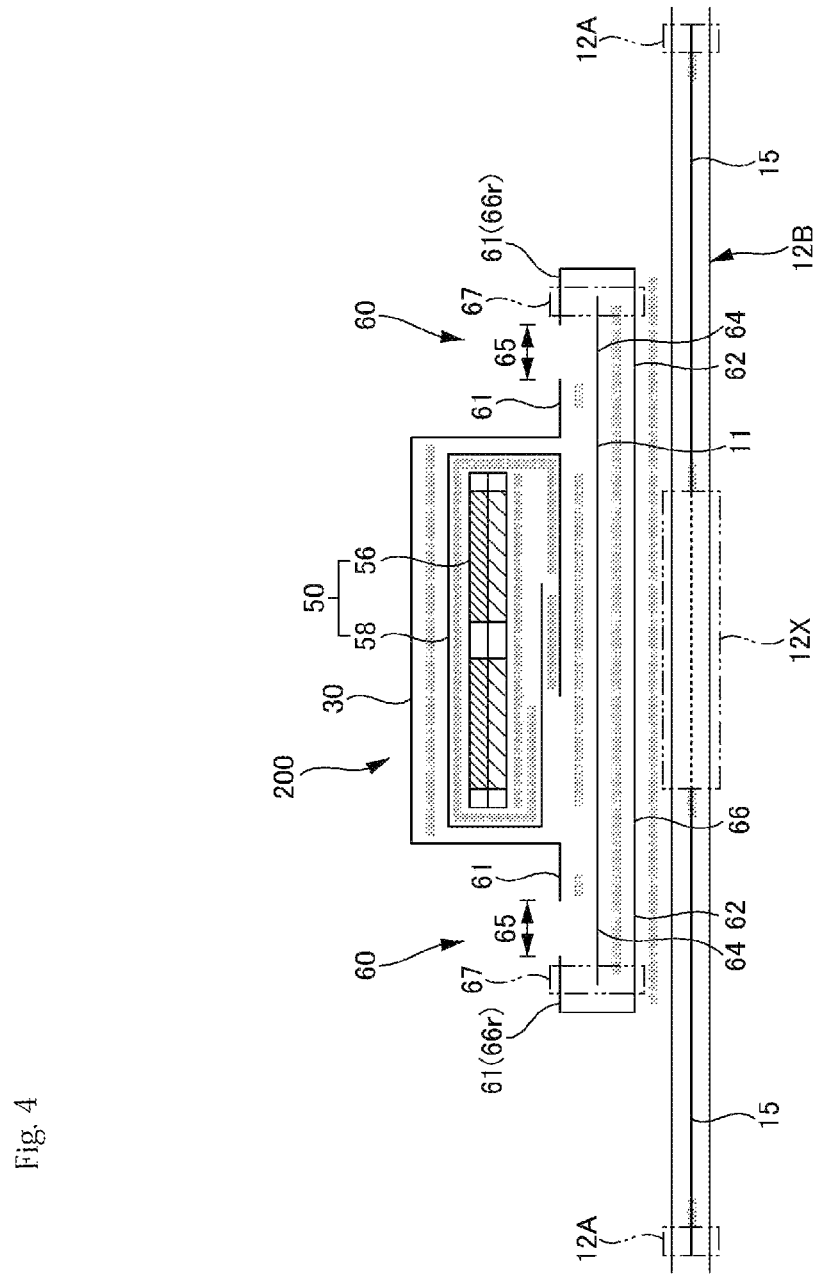
FIG. 4 is a cross-sectional view illustrating a layer configuration of 4-4 cross section of FIG. 1.
Figure 5:
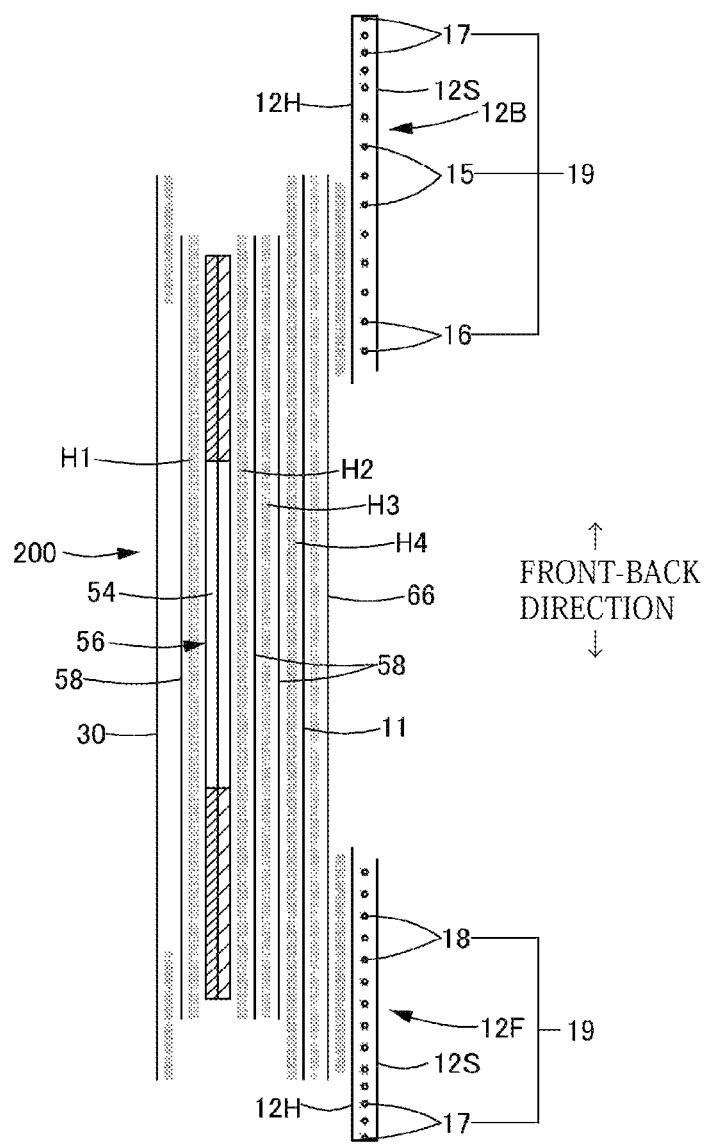
FIG. 5 is a cross-sectional view illustrating a layer configuration of 5-5 cross section of FIG. 1.

As illustrated in FIG. 2 to FIG. 5, the outer members 12F and 12B are formed by joining an outer sheet layer 12S and an inner sheet layer 12H using joining means such as a hot melt adhesive, welding, etc. In this way, a front surface and a back surface are formed. The outer sheet layer 12S and the inner sheet layer 12H may be formed by folding one sheet material such that a fold is located on the waist opening side as illustrated in FIG. 5, or may be formed by pasting two sheet materials together as illustrated in FIG. 10. In addition, in at least one of the outer sheet layer 12S and the inner sheet layer 12H, a part thereof may be formed by a different sheet material from that of another part.

As the sheet material used for the outer sheet layer 12S and the inner sheet layer 12H, any material may be used without particular restriction as long as the material has a shape of a sheet. However, a nonwoven fabric is preferably used. A raw material fiber of the nonwoven fabric is not particularly restricted. Examples thereof may include a synthetic fiber such as an olefin synthetic fiber such as polyethylene, polypropylene, etc., a polyester synthetic fiber, a polyamide synthetic fiber, etc., a regenerated fiber such as rayon or cupra, a natural fiber such as cotton, or a mixed fiber, a composite fiber, etc. using two types or more thereof. Further, the nonwoven fabric may be manufactured by any process. Examples of a processing method may include a known method such as a spun lace method, a spun bond method, a thermal bond method, a melt blown method, a needle-punch method, an air-through method, a point bond method, etc. In particular, in terms of flexibility, a nonwoven fabric such as an SMS nonwoven fabric, an SMMS nonwoven fabric, etc. formed by interposing a melt blown nonwoven fabric layer of one layer or a plurality of layers of a polypropylene ultrafine fiber between spun bond nonwoven fabric layers of a polypropylene fiber is suitable for the outer sheet layer 12S and the inner sheet layer 12H.

In the case of using the nonwoven fabric, a fineness is preferably set to about 0.5 to 2.5 dtex, and a basis weight is preferably set to about 10 to 30 g/m$^2$. Therefore, a total basis weight of the nonwoven fabric used for the outer members 12F and 12B is preferably about 20 to 60 g/m$^2$.

Further, an elongated elastically stretchable member 19 (15 to 18) such as a rubber thread is provided at a predetermined stretch rate in a stretchable structure-formed area in a waist direction between the outer sheet layer 12S and the inner sheet layer 12H in the outer members 12F and 12B. Synthetic rubber or natural rubber may be used as the elongated elastically stretchable member 19. At least one of a hot melt adhesive based on various application schemes and fixing means based on material welding such as heat sealing, ultrasonic sealing, etc. may be used for joining of the outer sheet layer 12S and the inner sheet layer 12H in the outer members 12F and 12B or fixing of the elongated elastically stretchable members 15 to 19 interposed therebetween. When the outer sheet layer 12S and the inner sheet layer 12H are joined on the entire surfaces of the outer members 12F and 12B, flexibility is impaired. Thus, it is preferable that the outer sheet layer 12S and the inner sheet layer 12H are intermittently joined in at least one of the front-back direction and the width direction (for example, the layers are not joined at a passing position of the elongated elastically stretchable member 19 or conversely the layers are joined only at the passing position). Both end portions of the elongated elastically stretchable member 19 in the width direction are fixed to the outer sheet layer 12S and the inner sheet layer 12H (fixing end portions). It is preferable that the elongated elastically stretchable member 19 is not joined to the outer sheet layer 12S and the inner sheet layer 12H between the fixing end portions in terms of flexibility. However, the elongated elastically stretchable member 19 may be joined therebetween. The illustrated mode corresponds to the latter, and the whole of the elongated elastically stretchable member 19 in a longer direction is fixed to the outer sheet layer 12S and the inner sheet layer 12H. When the elongated elastically stretchable member 19 is fixed to the outer sheet layer 12S and the inner sheet layer 12H using a hot melt adhesive, it is possible to use a scheme of applying the hot melt adhesive only to an outer peripheral surface of the elongated elastically stretchable member 19 by application means such as comb gun or Surewrap nozzle, etc. and interposing the elongated elastically stretchable member 19 between both the sheet layers 12S and 12H, or use a scheme of applying the hot melt adhesive to at least one of the outer sheet layer 12S and the inner sheet layer 12H and interposing the elongated elastically stretchable member 19 therebetween.

The illustrated mode will be described in more detail. First, a plurality of waist portion elastically stretchable members 17 is attached at an interval in an up-down direction and at a predetermined stretch rate in a stretched state along the width direction to be continuous over a whole in the width direction between the outer sheet layer 12S and the inner sheet layer 12H in the waist portion W of the outer members 12F and 12B. Among the waist portion elastically stretchable members 17, one or a plurality of members arranged in a region adjacent to the under-waist portion U may overlap with the inner member 200 or may be provided at each of both sides of a central portion in the width direction overlapping the inner member 200 except for the central portion. As the waist portion elastically stretchable members 17, it is preferable to attach about 3 to 22 rubber threads having a fineness of about 155 to 1880 dtex, particularly 470 to 1240 dtex (in the case of synthetic rubber. In the case of natural rubber, a cross-sectional area is about 0.05 to 1.5 mm$^2$, particularly 0.1 to 1.0 mm$^2$) at an interval of 4 to 12 mm such that each of the rubber threads has a stretch rate of about 150 to 400%, particularly 220 to 320%. In addition, not all the waist portion elastically stretchable members 17 may have the same fineness and stretch rate. For example, a fineness and a stretch rate of an elastically stretchable member may be different between an upper portion and a lower portion of the waist portion W.

In addition, in each part on an upper side and both sides in the width direction of a central portion overlapping the inner member 200 in the width direction except for the central portion between the outer sheet layer 12S and the inner sheet layer 12H in the under-waist portion U of the outer members 12F and 12B, a plurality of under-waist portion elastically stretchable members 15 and 18 including the elongated elastically stretchable member is attached at an interval in the up-down direction and at a predetermined stretch rate in a stretched state along the width direction to be continuous over the whole in the width direction.

As the under-waist portion elastically stretchable members 15 and 18, it is preferable to attach about 5 to 30 rubber threads having a fineness of about 155 to 1880 dtex, particularly 470 to 1240 dtex (in the case of synthetic rubber. In the case of natural rubber, a cross-sectional area is about 0.05 to 1.5 mm$^2$, particularly 0.1 to 1.0 mm$^2$) at an interval of 1 to 15 mm, particularly 3 to 8 mm such that each of the rubber threads has a stretch rate of about 200 to 350%, particularly 240 to 300%.

In addition, in each part on both sides in the width direction of a central portion overlapping the inner member 200 in the width direction except for the central portion between the outer sheet layer 12S and the inner sheet layer 12H in the gluteal region cover portion 14 of the back side outer member 12B, a plurality of cover portion elastically stretchable members 16 including the elongated elastically stretchable members is attached at an interval in the up-down direction and at a predetermined stretch rate in a stretched state along the width direction to be continuous over the whole in the width direction.

As the cover portion elastically stretchable members 16, it is preferable to attach about 2 to 10 rubber threads having a fineness of about 155 to 1880 dtex, particularly 470 to 1240 dtex (in the case of synthetic rubber. In the case of natural rubber, a cross-sectional area is about 0.05 to 1.5 mm$^2$, particularly 0.1 to 1.0 mm$^2$) at an interval of 5 to 40 mm, particularly 5 to 20 mm such that each of the rubber threads has a stretch rate of about 150 to 300%, particularly 180 to 260%.

When the inguinal cover portion is provided in the front side outer member 12F, the cover portion elastically stretchable member may be similarly provided.

When the elastically stretchable member 19 provided in the outer members 12F and 12B (the under-waist portion elastically stretchable members 15 and 18 and the cover portion elastically stretchable member 16 in the illustrated mode) is provided at each of both sides in the width direction of a portion overlapping the inner member 200 except for a part or a whole of the portion as in the illustrated mode, the inner member 200 does not contract in the width direction more than necessary, a poor appearance such as a lumpy appearance is not obtained, and absorbency is not reduced. In addition to a mode in which the elastically stretchable member 19 is present only at both sides in the width direction, this mode includes a mode in which the elastically stretchable member 19 is present across the inner member 200 from one side to the other side thereof in the width direction, the elastically stretchable member 19 is finely cut as indicated by reference symbol 12X in FIG. 2 and FIG. 4 in a widthwise intermediate portion or whole portion of a part overlapping the inner member 200, a contraction force does not act thereon (substantially, equivalent to a case in which the elastically stretchable member is not provided), and only both sides thereof in the width direction is configured as a contraction force acting part. An arrangement mode of the elastically stretchable member 19 provided in the outer members 12F and 12B is not limited to the above example. A portion or a whole of the elastically stretchable member 19 may be provided across the inner member 200 from one side to the other side thereof in the width direction such that a stretching force acts over a whole in the width direction including the part overlapping the inner member 200.

(Inner Member)

A shape and a structure of the inner member 200 are not particularly restricted. For example, a shape and a structure described below may be adopted. An arbitrary shape may be adopted for the inner member 200, and a rectangular shape is adopted in the illustrated mode. As illustrated in FIG. 3 to FIG. 5, the inner member 200 includes a liquid pervious top sheet 30 corresponding to a skin side of the wearer, a liquid impervious sheet 11, and an absorbent element 50 interposed therebetween, and corresponds to a main unit section having an absorbing function. Reference symbol 40 indicates an intermediate sheet (also referred to as a second sheet) provided between the top sheet 30 and the absorbent element 50 to promptly transfer a liquid permeating through the top sheet 30 to the absorbent element 50, and reference symbol 60 indicates a leg gather 60, which is a part rising toward the leg of the wearer, extending along both sides of an absorption surface of the inner member in the width direction to prevent excretion from leaking to both sides of the inner member 200.

(Top Sheet)

A material is used for the top sheet 30 without particular restriction as long as the material corresponds to a liquid pervious material such as a perforated or nonporous nonwoven fabric, a porous plastic sheet, etc. However, when the top sheet 30 also serves as a covering material for a liquid impervious sheet 64 of the leg gather 60 as in the mode illustrated in FIG. 3 and FIG. 4, a nonwoven fabric is used. In addition, a raw material fiber of the nonwoven fabric is not particularly restricted. Examples thereof may include a synthetic fiber such as an olefin synthetic fiber such as polyethylene, polypropylene, etc., a polyester synthetic fiber, a polyamide synthetic fiber, etc., a regenerated fiber such as rayon or cupra, a natural fiber such as cotton, or a mixed fiber, a composite fiber, etc. using two types or more thereof. Further, the nonwoven fabric may be manufactured by any process. Examples of a processing method may include a known method such as a spun lace method, a spun bond method, a thermal bond method, a melt blown method, a needle-punch method, an air-through method, a point bond method, etc. For example, when flexibility and draping are required, the spun bond method and the spun lace method are preferable processing schemes, whereas when bulkiness and softness are required, the air-through method, the point bond method, and the thermal bond method are preferable processing schemes.

In addition, the top sheet 30 may be made of one sheet or a stacked sheet obtained by bonding two or more sheets. Similarly, the top sheet 30 may be made of one sheet or two or more sheets in a plane direction.

Figure 7:
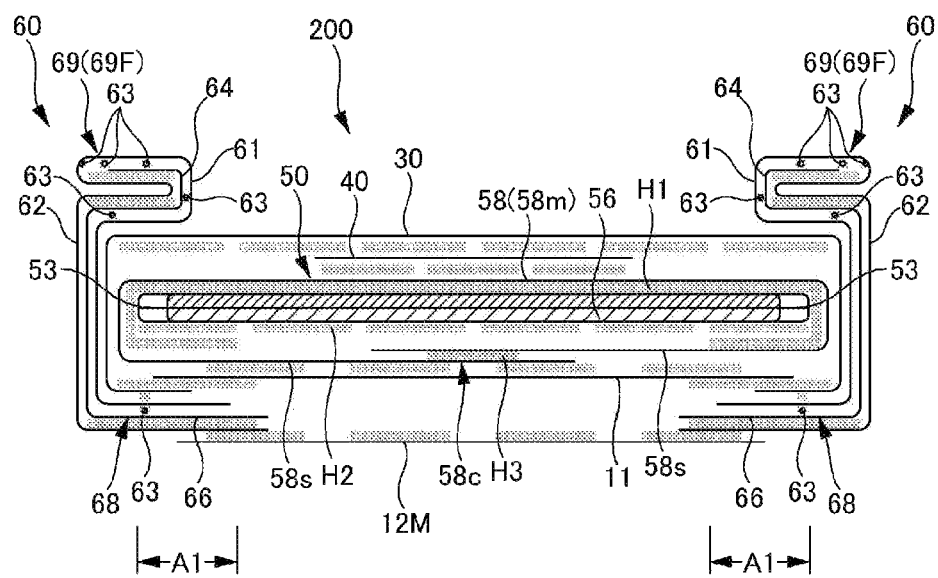
FIG. 7 is a cross-sectional view illustrating a layer configuration of a cross section corresponding to 3-3 cross section of FIG. 1.
Figure 8:
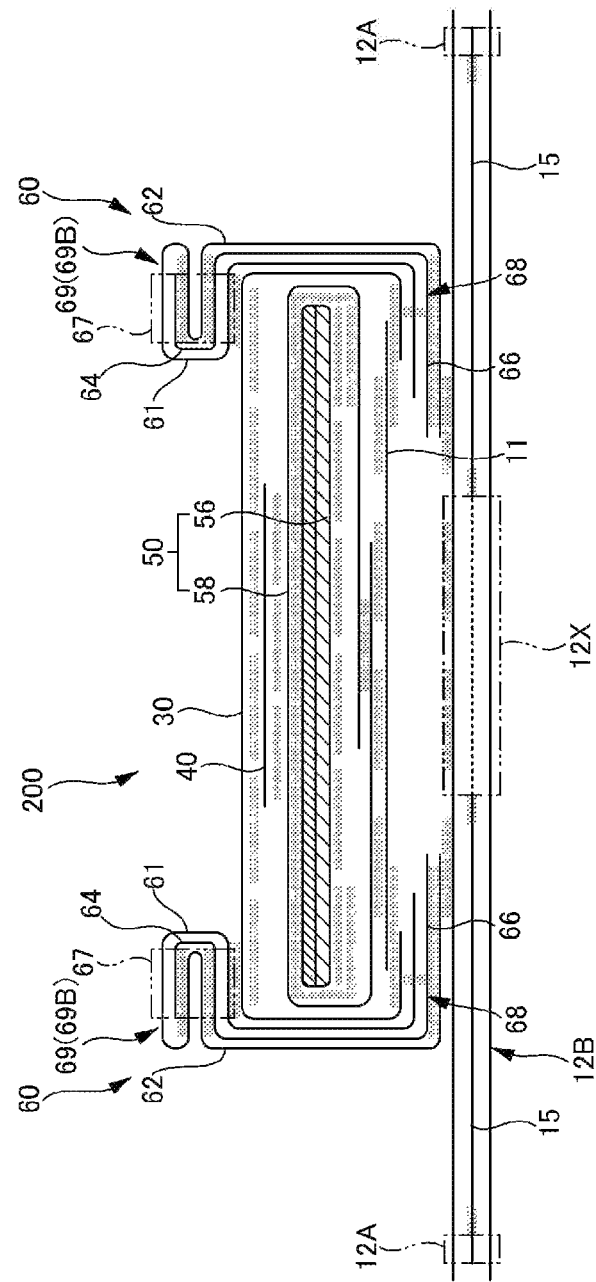
FIG. 8 is a cross-sectional view illustrating a layer configuration of a cross section corresponding to 4-4 cross section of FIG. 1.

If the both sides of the top sheet 30 in the width direction do not function as the covering material of the liquid impervious sheets 64 of the leg gathers 60, for example, the top sheet 30 can be passed between the absorbent element 50 and the leg gather 60 to the back face side of the absorbent element 50 and bonded to the liquid impervious sheet 11 and the leg gather 60 using a hot melt adhesive, etc. to prevent penetration of liquid as in the mode illustrated in FIG. 7 and FIG. 8.

(Intermediate Sheet)

As in the mode illustrated in FIG. 7 and FIG. 8, the intermediate sheet (also referred to as a "second sheet") 40 superior in hydrophilicity to the top sheet may be provided on the back face side of the top sheet 30. The intermediate sheet 40 is provided to prevent a returning phenomenon of an absorbed liquid from the absorbent body and to ensure a smooth touch on the top sheet 30. The intermediate sheet 40 may be omitted.

Examples of the intermediate sheet 40 may include a similar material to that of the top sheet 30, spun lace, spun bond, SMS, pulp nonwoven fabric, a mixed sheet of pulp and rayon, point bond or crepe tissue. In particular, air-through nonwoven fabric is bulky, and thus is preferable. It is preferable to use a composite fiber having a core-sheath structure for the air-through nonwoven fabric. In this case, a resin used for a core may be polypropylene (PP). However, polyester (PET) having high rigidity is preferable. A basis weight is preferably 20 to 80 $g/m^2$, more preferably 25 to 60 $g/m^2$. A fineness of a raw material fiber of the nonwoven fabric is preferably 2.2 to 10 dtex. In order to increase the bulkiness of the nonwoven fabric, it is preferable to use an eccentric fiber having no core in a center, a hollow fiber, and an eccentric and hollow fiber as a mixed fiber of a whole or a part of the raw material fiber.

The intermediate sheet 40 of the illustrated mode is shorter than a width of the absorbent body 56 and disposed at a center. However, the intermediate sheet 40 may be provided over the maximum width of the absorbent body. A length of the intermediate sheet 40 in the longer direction may be equal to a length of the absorbent body 56 or within a short length range centered on a region in which a liquid is received.

(Liquid Impervious Sheet)

A material of the liquid impervious sheet 11 provided on the back face side of the absorbent body 56 is not particularly limited. However, examples thereof may include a plastic film made of an olefin resin such as polyethylene, polypropylene, etc. A material having liquid impermeability and moisture permeability which has been recently favorably used from the viewpoint of prevention of unevenness is preferably used for the liquid impervious sheet 11. A microporous plastic film obtained by kneading an inorganic filler in an olefin-based resin such as polyethylene or polypropylene, molding a sheet, and then performing stretching in a monoaxial or biaxial direction is widely used as the plastic film having moisture permeability.

The liquid impervious sheet 11 may be allowed to serve as the liquid pervious film 64 in the leg gather 60 by being laterally extended beyond the absorbent body 56 as in the mode illustrated in FIG. 3 and FIG. 4, may be set to have a width fit to the back face side of the absorbent element 50 as illustrated in FIG. 7 and FIG. 8, or may be extended up to both side portions of a surface of the absorbent element 50 on the top sheet 30 side by being wrapped around the both sides of the absorbent element 50 in the width direction.

In addition, it is possible to provide an excretion indicator whose color changes due to absorption of a liquid component on the inside of the liquid impervious sheet 11, particularly a surface on the absorbent body 56 side.

(Absorbent Element)

The absorbent element 50 includes the absorbent body 56 and a wrapping sheet 58 wrapping the entire absorbent body 56.

(Absorbent Body)

The absorbent body 56 is obtained by mixing and accumulating pulp fibers, synthetic fibers, etc. and high absorbent polymer particles. In a case of stacking cotton-like pulp fibers or short fibers, for example, a fiber basis weight of the absorbent body 56 may be set to about 100 to 300 $g/m^2$. In a case of using synthetic fibers, for example, a fineness thereof may be set to 1 to 16 dtex, preferably 1 to 10 dtex, more preferably 1 to 5 dtex.

Figure 6:
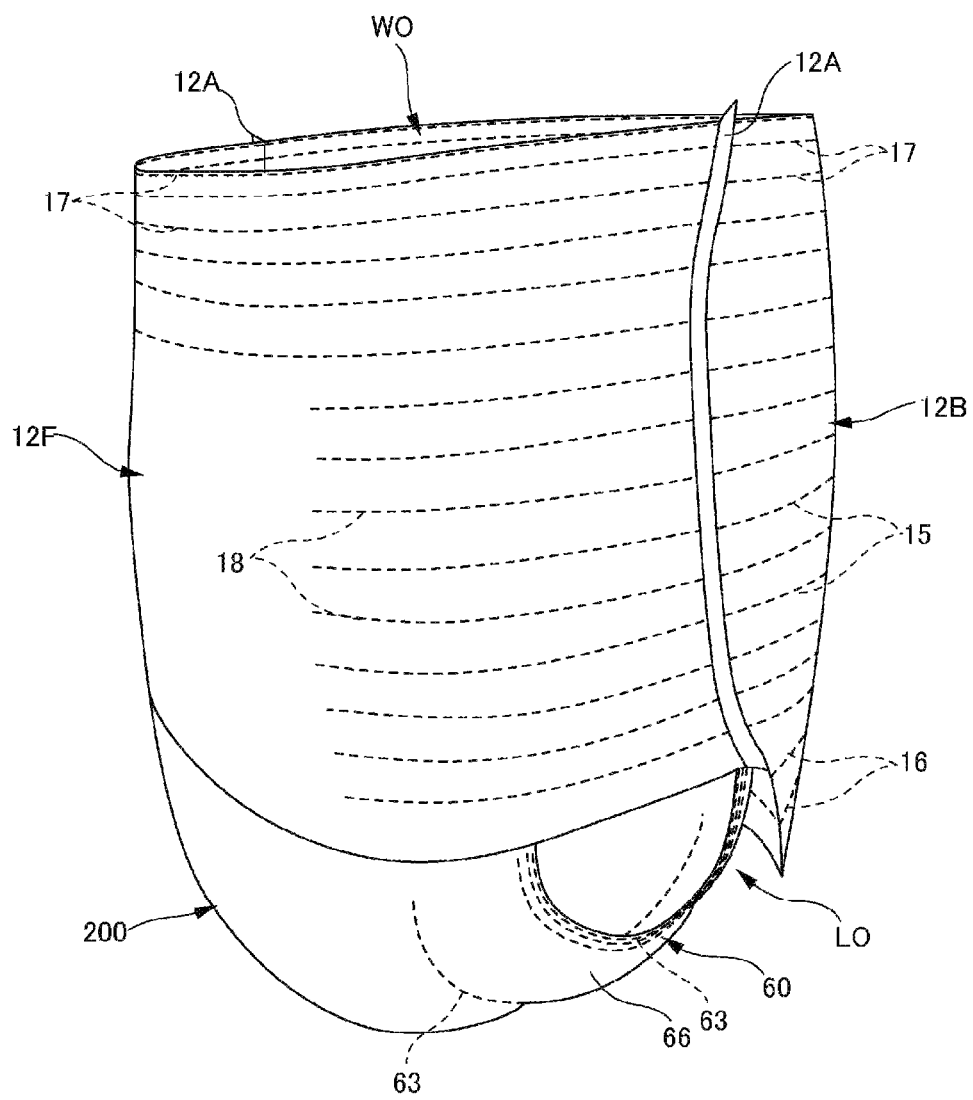
FIG. 6 is a perspective view of the underpants-type disposable diaper.

The absorbent body 56 may have a rectangular shape. However, when an hourglass shape whose width is narrower than widths of both front and back sides is formed due to the narrowing portions 53 in a middle in the front-back direction as illustrated in FIG. 6, a fitting property of the absorbent body 56 and the leg gather 60 with respect to the leg is improved, and thus the hourglass shape is preferable. In addition, in the absorbent body 56, a slit 54 penetrating therethrough in the thickness direction may be extended in the front-back direction in order to improve liquid diffusibility in the front-back direction. As long as the slit 54 is provided in the crotch portion, a length thereof in the front-back direction is not particularly restricted. Therefore, the slit 54 may be provided across the whole absorbent body 56 in the front-back direction. However, it is desirable that the slit 54 is extended from a front side to a back side of the crotch portion as in the illustrated mode. It is preferable that one or two linear slits 54 are provided. However, three or more slits may be provided, and the slit may have a curved shape.

Dimensions of the absorbent body 56 may be appropriately determined. However, it is preferable that the absorbent body 56 extends to a peripheral edge portion of the inner member 200 or to the vicinity thereof in the front-back direction and the width direction. Reference numeral 56x indicates the width of the absorbent body 56.

High absorbent polymer particles are mixed and contained in a part or a whole of the absorbent body 56. The high absorbent polymer particle includes "powder" in addition to a "particle". A particle used in this type of absorbent article may be used as the high absorbent polymer particle without change. For example, it is desirable that the proportion of particles remaining on the sieve is 30% by weight or less by sieving (shaking for 5 minutes) using a 500 μm standard sieve (JIS Z 8801-1: 2006), and it is desirable that the proportion of particles remaining on the sieve is 60% by weight or more by sieving (shaking for 5 minutes) using a 180 μm standard sieve (JIS Z 8801-1: 2006).

A material of the high absorbent polymer particle may be used without particular limitation. However, a material having a water absorption amount (JIS K7223-1996 "Testing method for water absorption capacity of super absorbent polymers") of 40 g/g or more is suitable. Examples of the high absorbent polymer particle include starch-based, cellulose-based and synthetic polymer-based ones, and it is possible to use a starch-acrylic acid (salt) graft copolymer, a saponified starch-acrylonitrile copolymer, crosslinked sodium carboxymethylcellulose, an acrylic acid (salt) polymer, etc. A normally used granular shape is suitable for a shape of the high absorbent polymer particle. However, another shape may be used.

A particle having a water absorption rate of 70 seconds or less, particularly 40 seconds or less is suitably used as the high absorbent polymer particle. When the water absorption rate is excessively low, so-called returning, in which a liquid supplied into the absorbent body 56 returns to the outside of the absorbent body 56, is likely to occur.

A basis weight amount of the high absorbent polymer particle may be appropriately determined according to the absorption amount required for the use of the absorbent body 56. Therefore, even though it cannot be said unconditionally, the basis weight amount may be set to 50 to 350 $g/m^2$. When the basis weight amount of the polymer is less than 50 $g/m^2$, it is difficult to ensure the absorption amount. When the basis weight amount exceeds 350 $g/m^2$, the effect is saturated.

It is presumed that a total weight of high absorbent polymer particles is larger than a total weight of fibers in the absorbent body 56. A weight ratio of fibers:high absorbent polymer particles in the absorbent body 56 preferably corresponds to 50:50 to 20:80, particularly 40:60 to 20:80. In this way, when comparison is performed at the same area and the same absorption amount, the thinner absorbent body 56 may be obtained. In this case, a thickness 56t of the absorbent body 56 is not particularly limited. However, the thickness may be set to 3 to 15 mm.

Figure 12:
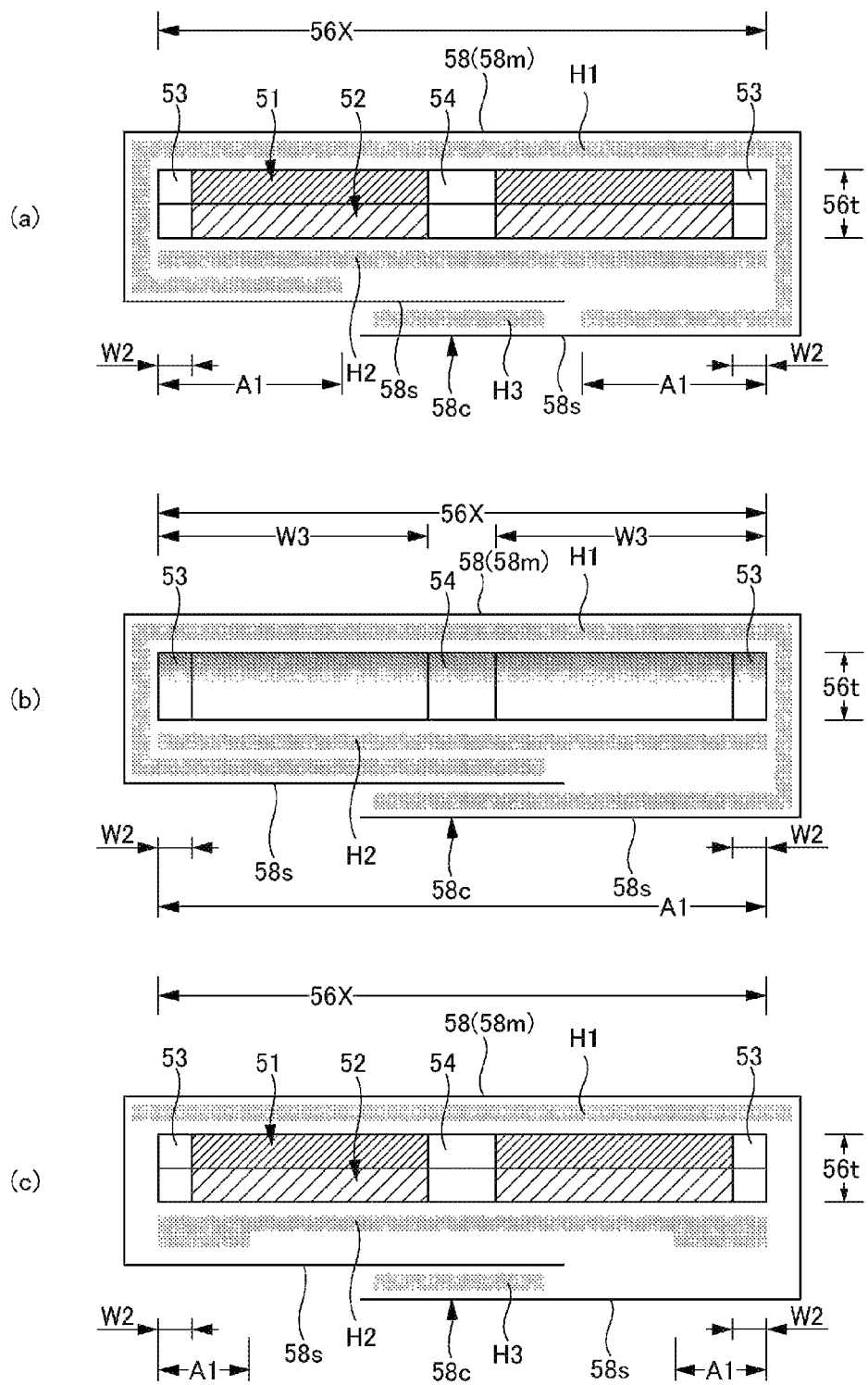
FIG. 12 is a cross-sectional view illustrating a layer configuration of an absorbent element.

In addition, the content rate (weight percentage) of the high absorbent polymer particles in the absorbent body 56 increases stepwise or continuously from the back face side to the front face side. In this way, prevention of returning known as a phenomenon in which liquid content of excretion entering the absorbent body 56 side returns to the skin side is excellent. Stepwise changing of the content rate of the high absorbent polymer particles refers to a state in which a plurality of layers 51 and 52 having different content rates as in the absorbent body 56 illustrated in FIG. 12(a) is stacked, and the content rates are substantially constant in the respective layers 51 and 52. Further, continuous changing refers to a state (indicated by gradation in the figure) of not having a layered structure in which a content rate changes stepwise as in the absorbent body 56 illustrated in FIG. 12(b). In addition, "stepwise or continuous increasing" of the content rate of the high absorbent polymer particles in the absorbent body 56 includes a mode in which a layer not containing the high absorbent polymer particles (a layer having a content rate of 0) is included on one side of the front face side and back face side of the absorbent body, and the content rate increases therefrom in addition to a mode in which the high absorbent polymer particles are included in the whole of the absorbent body in the thickness direction.

When the content rate of the high absorbent polymer particles is changed stepwise, the number of layers having a substantially constant content rate is not particularly limited, and a thickness of each layer is not particularly limited. For example, in a case of adopting a two-layered structure including a high content rate layer 51 and a low content rate layer 52 as illustrated in FIG. 12(a) for the purpose of prevention of returning while adopting a thin absorbent body in which a total weight of high absorbent polymer particles is larger than a total weight of fibers as described above, it is preferable that a content rate of high absorbent polymer particles in the high content rate layer 51 is set to 50 to 90% by weight, and a content rate of high absorbent polymer particles in the low content rate layer 52 is set to 15 to 60% by weight. In addition, it is preferable that a thickness of the high content rate layer 51 is set to 20 to 60% of the thickness 56*t* of the absorbent body 56, and a thickness of the low content rate layer 52 is set to 40 to 80% of the thickness 56*t* of the absorbent body 56.

As necessary, the content rate of the high absorbent polymer particles may be changed in the plane direction of the absorbent body 56. For example, the amount of a liquid excretion part may be increased more than the amount of other parts. In a case of considering a difference between men and women, it is possible to raise the content rate on the front side for men and to raise the content rate in the central part for women. Further, it is possible to provide a portion in which no polymer is present locally (for example, in a spot shape) in the plane direction of the absorbent body 56.

(Wrapping Sheet)

It is possible to use a liquid pervious material such as tissue paper, particularly crepe tissue, nonwoven fabric, poly-laminate nonwoven fabric, a sheet having an open small hole, etc. as the material of the wrapping sheet 58. However, it is desirable that the high absorbent polymer particles do not come off from the sheet. When a nonwoven fabric is used in place of crepe tissue, a hydrophilic SMS nonwoven fabric (SMS, SSMMS, etc.) is particularly suitable, and polypropylene, polyethylene/polypropylene composite material, etc. may be used as the material. It is desirable that a basis weight is 5 to 40 g/m$^2$, particularly 10 to 30 g/m$^2$.

Figure 11:
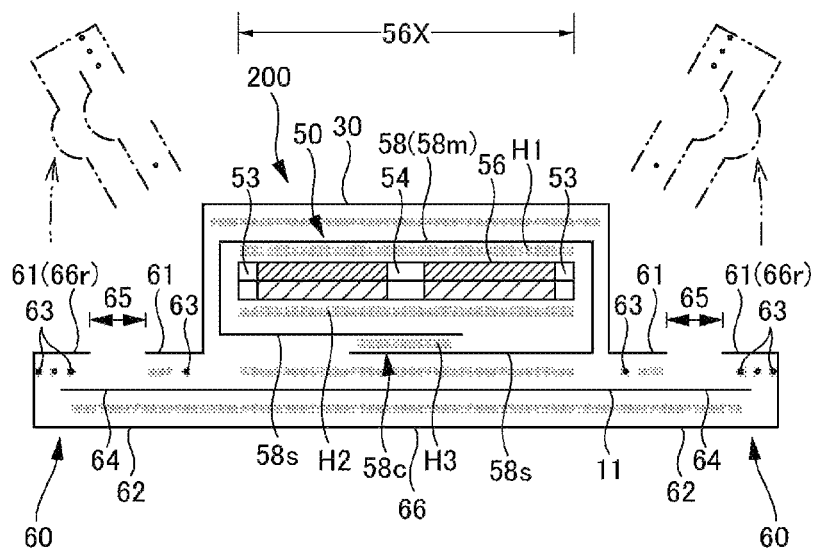
FIG. 11 is a cross-sectional view illustrating a layer configuration of a cross section corresponding to 3-3 cross section of FIG. 1.

A wrapping mode of the wrapping sheet 58 is set to a winding mode in which winding is performed in a barrel shape to surround the front surface and back surface and both side surfaces of the absorbent body 56 as illustrated in FIG. 3, FIG. 7 and FIG. 11 from viewpoints of ease of manufacturing, prevention of leakage of the high absorbent polymer particles from front and back end edges, etc. More specifically, the wrapping sheet 58 includes an intermediate part 58*m* located on the front face side of the absorbent body 56 and both side parts 58*s* folded back from the intermediate part 58*m* to the back face side of the absorbent body 56, and distal ends of the both side parts 58*s* of the wrapping sheet 58 are overlapped on the back face side of the absorbent body 56 to form a connecting portion 58*c*. Front and back end portions of the wrapping sheet 58 extend beyond the front and the back of the absorbent body 56, and are directly joined at this extended part without interposing the absorbent body 56 therebetween.

Even when adhesion of the connecting portion 58*c* of the wrapping sheet 58 is insufficient, since the connecting portion 58*c* is located on the back face side of the absorbent body 56, that is, on an opposite side from a part in which the content rate of the high absorbent polymer particles in the absorbent body 56 is high, the high absorbent polymer particles rarely leak out. In addition, even when high absorbent polymer particles leaving the absorbent body 56 leak out from the connecting portion 58*c* of the wrapping sheet 58, this happens at the back face side of the absorbent element 50, and thus risk of leakage to the skin side of the wearer is small. Further, the overlapping part of the wrapping sheet 58 has higher liquid retentivity than that of another part. Thus, when the overlapping part is located on the front face side of the absorbent body 56, there is concern that returning may be promoted. However, when the overlapping part is located on the back face side of the absorbent body 56, such a problem does not occur.

(Adhesive Structure of Wrapping Sheet and Absorbent Body)

An internal surface of the wrapping sheet 58 is, at a whole part facing the absorbent body 56, bonded to an external surface of the absorbent body 56 through hot melt adhesives H1 and H2. In addition, an overlapping part of end portions of the wrapping sheet 58 in the connecting portion 58*c* are joined through a hot melt adhesive H3.

Figure 13:
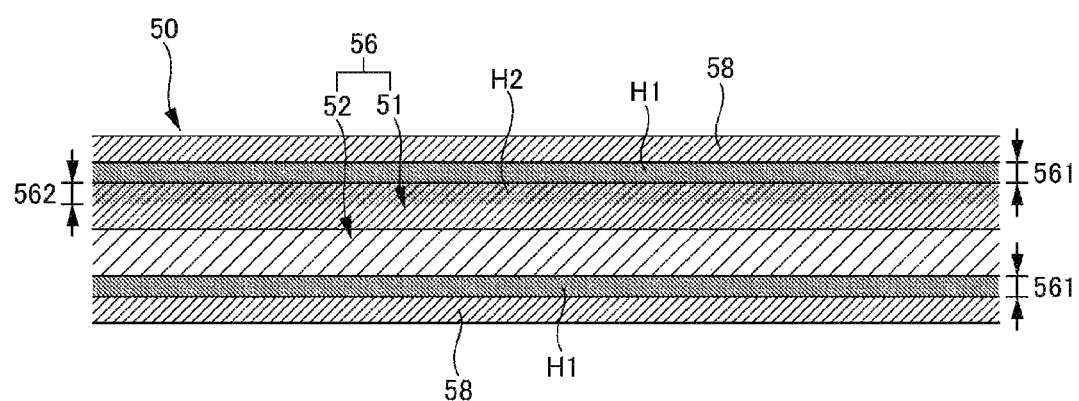
FIG. 13 is a cross-sectional view of the absorbent element.
Figure 13:
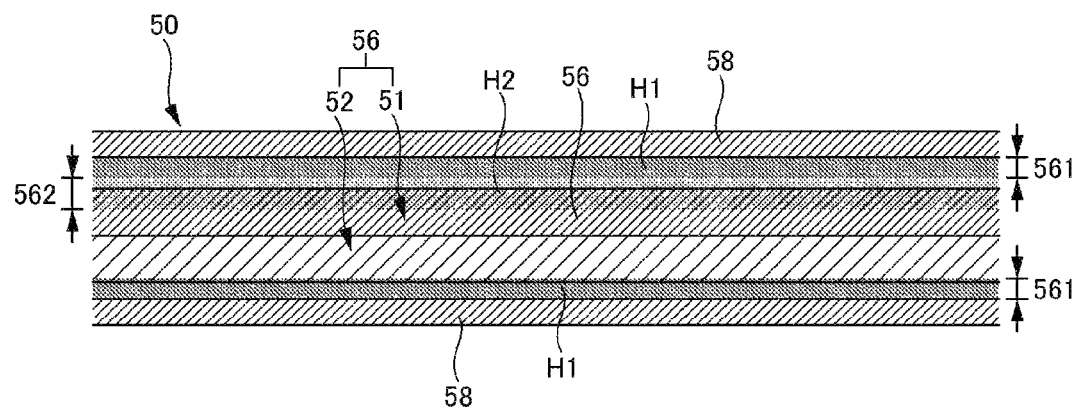

Even though the usage amount of the hot melt adhesives H1 and H2 bonding the wrapping sheet 58 and the absorbent body 56 together is not particularly limited, the usage amount is preferably larger in a region A1 of at least both end portions in the width direction on the side of the absorbent body having the connecting portion 58*c* of the wrapping sheet 58 than on the opposite side of the absorbent body 56. In this way, as described above, it is possible to enhance an adhesive force of the wrapping sheet 58 and the absorbent body 56 on a side where the adhesive force is likely to decrease (the side having the connecting portion 58*c*), and to effectively suppress deformation of the shape of the absorbent body 56 while suppressing the total usage amount of the hot melt adhesives H1 and H2 for bonding the absorbent body 56 and the wrapping sheet 58. It is desirable that the hot melt adhesives H1 and H2 bonding the wrapping sheet 58 and the absorbent body 56 penetrate the absorbent body 56 together to some extent as illustrated in FIG. 13 to form an impregnation layer 562 and hardly penetrate the wrapping sheet 58 or penetrate the wrapping sheet 58 less than the absorbent body 56 to form an adhesive layer 561.

The usage amount of the hot melt adhesives H1 and H2 bonding the wrapping sheet 58 and the absorbent body 56 together may be appropriately determined. However, it is preferable to set the amount to a range of 12 to 25 g/m$^2$ in a large amount region A1 and to a range of 9 to 15 g/m$^2$ in a small amount region (a region outside of the region A1). In addition, it is preferable to set the usage amount in the large amount region A1 to 1.1 to 1.4 times the usage amount in the small amount region. As in the mode illustrated in FIG. 11, the usage amount of the hot melt adhesives bonding the wrapping sheet 58 and the absorbent body 56 together may be made equal on both front face side and back face side of the absorbent body 56 (the large amount region A1 is not formed). In this case, even though the usage amount of the hot melt adhesives H1 and H2 bonding the wrapping sheet 58 and the absorbent body 56 together is not particularly limited, the usage amount is preferably within a range of 2 to 10 g/m$^2$.

In particular, when a total weight of high absorbent polymer particles is larger than a total weight of fibers in the absorbent body 56 (that is, a content rate of the high absorbent polymer particles is high in the absorbent body 56) as described above, shape deformation of the both end portions of the absorbent body 56 in the width direction is likely to occur, and thus it is preferable to reinforce such hot melt adhesives H1 and H2 using the large amount region A1.

In addition, when the narrowing portions 53 for improving a fitting property around the legs are formed in the absorbent body 56 as in the illustrated mode, shape deformation is likely to occur at the narrowing portions 53. Thus, in a preferable mode, the large amount region A1 of the hot melt adhesives H1 and H2 is set to a region including the whole narrowing portions 53 in the width direction to suppress shape deformation of the absorbent body 56 at the narrowing portions 53.

Similarly, in a mode in which the slit 54 penetrating the absorbent body 56 in the thickness direction extends in the front-back direction in the intermediate portion of the absorbent body 56 in the width direction as illustrated in FIG. 12(b), shape deformation in the slit 54 is likely to occur. Thus, in a preferable mode, the large amount region of the hot melt adhesives H1 and H2 is set to a region including the whole slit 54 in the width direction to suppress shape deformation of the absorbent body 56 in the slit 54.

The usage amount of the hot melt adhesives H1 and H2 may be changed by changing the application amount in one application for each part as illustrated in FIG. 12(c). However, since such a treatment is often difficult, it is preferable to create the usage amount by changing the number of stacked layers (that is, the number of overlapping coatings) of the hot melt adhesives H1 and H2 for each part as in the mode illustrated in FIG. 3, FIG. 7, and FIGS. 12(a) and 12(b).

In addition, when the usage amount of the hot melt adhesives H1 and H2 is changed based on the number of stacked layers of the hot melt adhesives H1 and H2, it is a preferred mode to make at least one of an application pattern and a type different depending on the coating layer. In this way, it is possible to locally increase the usage amount of the hot melt adhesives H1 and H2 while changing the application pattern or the type of the hot melt adhesives H1 and H2 depending on the application target in a simple manufacturing process.

In particular, as illustrated in FIG. 13, in a preferable mode, the absorbent body 56 has the impregnation layer 562 impregnated with the hot melt adhesive H2 having melt viscosity of 1,000 to 6,000 mPa·s (preferably 2,000 to 5,500 mPa·s) on a side having the connecting portion 58c, a part of the internal surface of the wrapping sheet 58 facing the impregnation layer 562 is bonded to the external surface of the impregnation layer 562 through the adhesive layer 561 made of the hot melt adhesive H1 having melt viscosity of 4,000 to 9,000 mPa·s (preferably 6,000 to 8,000 mPa·s), and the hot melt adhesive H2 impregnated into the impregnation layer 562 has lower viscosity than that of the hot melt adhesive H1 in the adhesive layer 561. A part of the absorbent body 56 not having the impregnation layer 562 may be bonded to the internal surface of the wrapping sheet 58 only through the adhesive layer 561. In this way, by adopting a structure in which the hot melt adhesives H1 and H2 having different melt viscosities are used at suitable right places as described above, in forming the impregnation layer 562, it is possible to effectively stabilize the shape of the absorbent body 56 by sufficient impregnation in the absorbent body 56 due to sufficiently low melt viscosity of the hot melt adhesive H2. Further, in forming the adhesive layer 561, permeation into the absorbent body 56 and the wrapping sheet 58 is difficult and adhesive properties of the absorbent body 56 and the wrapping sheet 58 are improved due to high melt viscosity of the hot melt adhesive H1. Therefore, it is possible to suppress the shape deformation of the absorbent body 56.

As illustrated in FIG. 13, the hot melt adhesive H2 is impregnated into the absorbent body 56, and the impregnation layer 562 is formed in a range up to a certain depth from an impregnation surface. A thickness of the impregnation layer 562 is not particularly limited. However, the thickness is preferable about 10 to 50% of the thickness 56t of the absorbent body 56. The whole hot melt adhesive H2 of the impregnation layer 562 in the thickness direction may permeate into the absorbent body 56 as illustrated in FIG. 13(a), and a part of the hot melt adhesive H2 in the thickness direction may remain on the absorbent body 56 as illustrated in FIG. 13(b).

As illustrated in FIG. 13, the adhesive layer 561 is a layer of the hot melt adhesive H1 located mainly between the wrapping sheet 58 and the impregnation layer 562 of the absorbent body 56, and is a layer which impregnates the wrapping sheet 58 to some extent. A part having the impregnation layer 562 is hardly impregnated into the absorbent body 56, and a part not having the impregnation layer 562 is impregnated into the absorbent body 56 more than the part having the impregnation layer 562.

Compositions of the hot melt adhesive H2 of the impregnation layer 562 and the hot melt adhesive H1 of the adhesive layer 561 are not particularly restricted as long as the melt viscosity is within the above range. However, it is preferable to use a rubber-based hot melt adhesive from the viewpoint of softness and odor. In addition, it is preferable that a functional group that increases polarity is imparted to the hot melt adhesive. When the polarity of the hot melt adhesive increases, it is possible to strengthen adhesion to the pulp fibers/the high absorbent polymer/the wrapping sheet 58 in a wet state by an intermolecular force. Further, a delayed crystalline type adhesive is preferably used as the hot melt adhesive H2 of the impregnation layer 562. The delayed crystalline type adhesive refers to a hot melt adhesive having a property of not crystallizing immediately after application and solidifying after penetrating between the fibers. When a highly viscous and delayed crystalline type hot melt adhesive is applied to the wrapping sheet 58, a large amount of application rarely causes exudation, penetration to the absorbent body 56 side occurs over time, and it is possible to increase adhesive strength of the wrapping sheet 58 and the absorbent body 56.

(Method of Manufacturing Absorbent Element)

Figure 14:
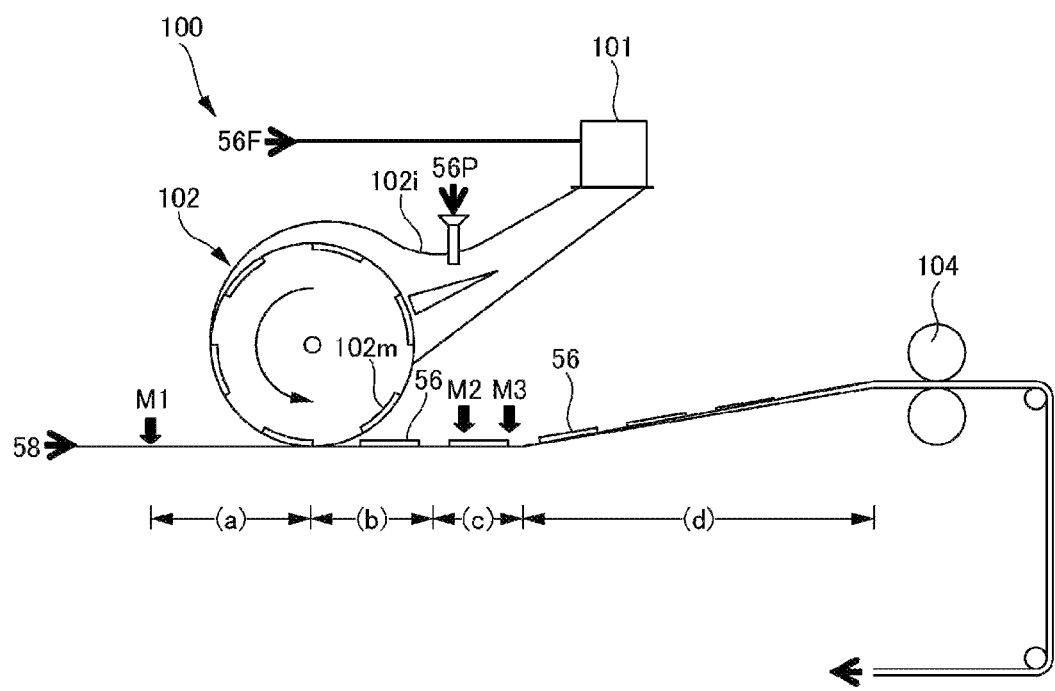
FIG. 14 is a schematic view illustrating a manufacturing facility for the absorbent element.
Figure 15:
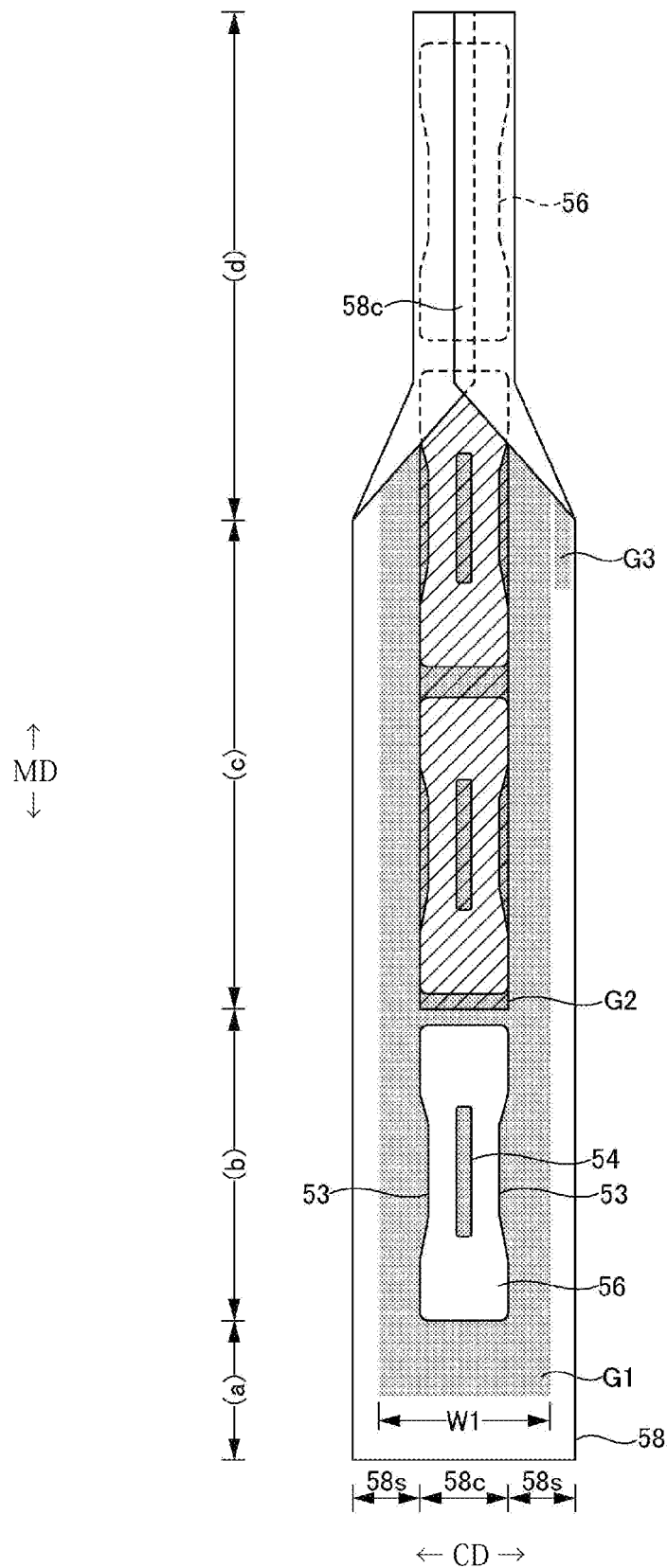
FIG. 15 is a plan view illustrating a manufacturing process of the absorbent element.
Figure 16:
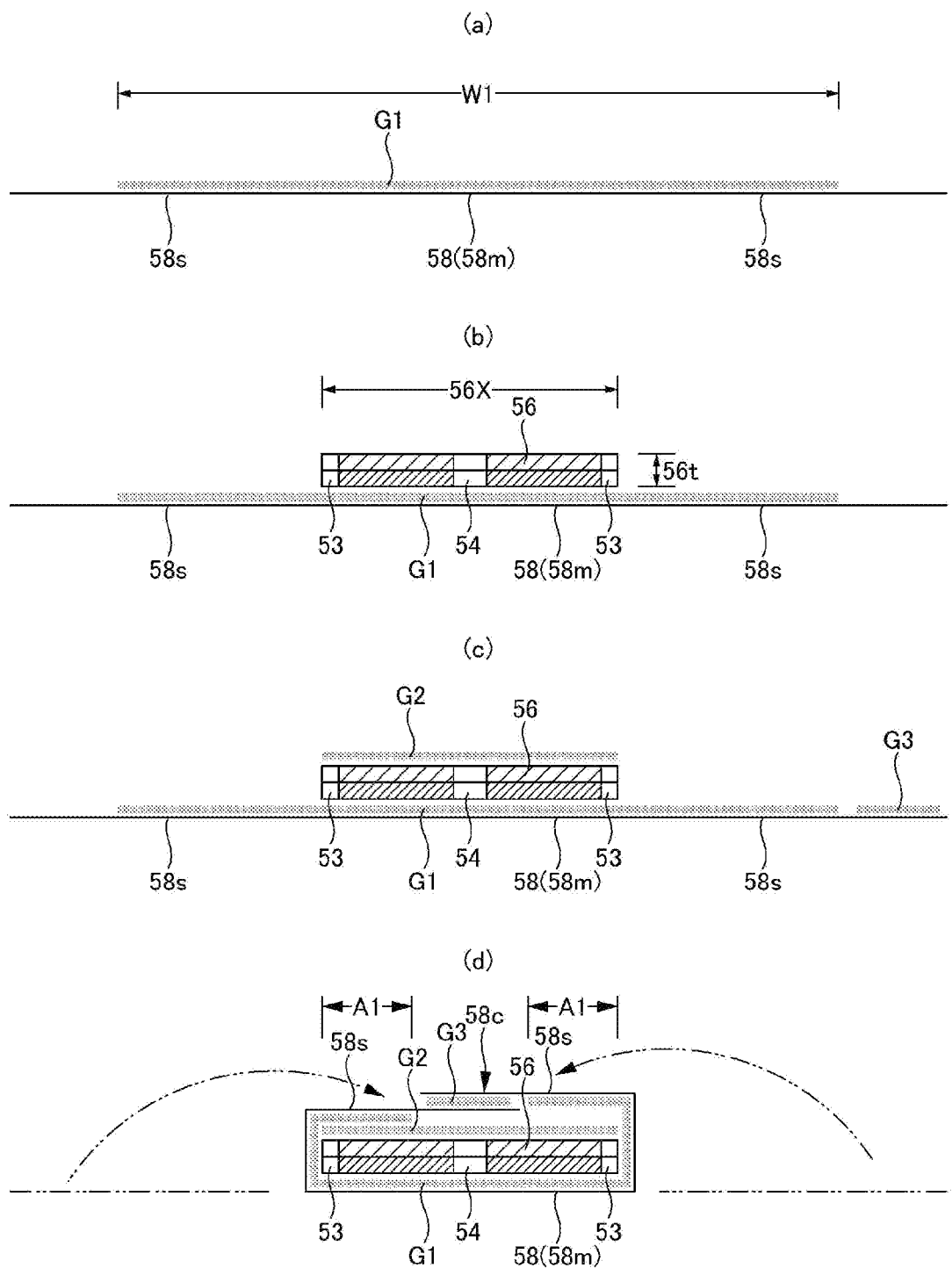
FIG. 16 is a cross-sectional view illustrating the manufacturing process of the absorbent element.

FIG. 13 to FIG. 15 illustrate an example of a facility/process for manufacturing the above-described absorbent element 50. Sections (a) to (d) illustrated in FIG. 13 and FIG. 14 correspond to cross-sectional states of (a) to (d) illustrated in FIG. 16. In this manufacturing facility 100, first, pulp fibers obtained by defibrating a pulp sheet 56F using a defibrating machine 101 and high absorbent polymer particles 56P are supplied from above a fiber accumulating drum 102 which is laterally disposed and rotationally driven. Absorbent body molds 102m each of which has a rotation direction corresponding to the front-back direction are formed in a concave shape on an outer peripheral surface of the fiber accumulating drum 102, a plurality of suction holes (not illustrated) is formed in a bottom face of each absorbent body mold 102m, and a mixture of the pulp fibers and the high absorbent polymer particles is accumulated in the absorbent body mold 102m by suction from the suction holes in the absorbent body mold 102m to form the absorbent body 56 at a feed location of the pulp fibers and the high absorbent polymer particles.

When a fiber supply path 102i with respect to the fiber accumulating drum 102 is divided into a plurality of pieces in a rotation direction of the drum, a supply amount of a high absorbent polymers is made different for each supply path, and a clearance between an outlet of each supply path and the outer peripheral surface of the drum is changed, it is possible to change the content rate of the high absorbent polymer particles in accumulation in each absorbent body mold 102m stepwise or continuously. In the illustrated mode, the fiber supply path 102i with respect to the fiber accumulating drum 102 is divided into two pieces in the rotation direction of the drum, and the high absorbent polymer 56P is supplied only to a supply path on the rotation direction side, thereby forming a layer substantially containing no high absorbent polymer particles 56P on a bottom portion side (suction hole side) in the absorbent body mold 102$m$, and forming a layer containing the high absorbent polymer particles 56P on an inlet side of the absorbent body mold 102$m$. There is an advantage that it is difficult for the high absorbent polymer particles 56P to be clogged in the suction holes of the absorbent body mold 102$m$.

The absorbent body 56 formed in the absorbent body mold 102$m$ is demolded from the mold and transferred onto the wrapping sheet 58 when the absorbent body 56 is located at a position facing the continuum-shaped wrapping sheet 58 supplied along the outer peripheral surface of the fiber accumulating drum 102 by rotation of the fiber accumulating drum 102. A first adhesive layer G1 is formed on a transfer surface of the wrapping sheet 58 for the absorbent body 56 by applying the hot melt adhesive M1 in advance, and the absorbent body 56 is bonded to the wrapping sheet 58 by the first adhesive layer G1. When this first bonding process is successively performed, the absorbent body 56 is intermittently supplied onto the continuously conveyed wrapping sheet 58, and adhesion is successively performed.

The width of the wrapping sheet 58 in the CD orthogonal to the MD (a conveying direction of the sheet) is wider than that of the absorbent body 56. After the absorbent body 56 is transferred onto an intermediate part 58$m$ in the CD, a second adhesive layer G2 is formed over the maximum width of an upper surface of the absorbent body 56 by applying a hot melt adhesive M2. The second adhesive layer G2 is an adhesive layer mainly intended to increase shape maintainability of the absorbent body 56 by being impregnated into the absorbent body 56. However, the second adhesive layer G2 also functions as an adhesive for the wrapping sheet 58. In addition, as necessary, a third adhesive layer G3 for bonding the connecting portion by applying a hot melt adhesive M3 is formed at one end portion of the wrapping sheet in the CD.

When accumulation is performed such that a large amount of the high absorbent polymer particles 56P is contained on a bottom side of each absorbent body mold 102$m$ in the fiber accumulating drum 102 and the high absorbent polymer particles 56P are transferred onto the wrapping sheet 58 (in this instance, upper and lower sides of the absorbent body 56 are switched) before application of the hot melt adhesive M2 for forming the second adhesive layer G2, a large amount of the high absorbent polymer particles 56P is contained on the upper surface side of the absorbent body 56. Thus, there is a problem that when the hot melt adhesive M2 is applied to the upper surface of the absorbent body 56, the high absorbent polymer particles 56P are likely to scatter due to an application force thereof. On the other hand, when accumulation is performed such that the content rate of the high absorbent polymer particles increases stepwise or continuously from the bottom side toward the inlet side of the absorbent body mold 102$m$ in the fiber accumulating drum 102, and the hot melt adhesive M2 is applied to the upper surface of the absorbent body 56, the content rate of the high absorbent polymer particles 56P decreases toward the upper surface side of the absorbent body 56, and the high absorbent polymer particles rarely scatter.

After application of the second adhesive layer G2, both side parts 58$s$ of the wrapping sheet 58 in the CD extending beyond both sides of the absorbent body 56 are folded back at positions along both side edges of the absorbent body 56 and bonded to the upper face of the absorbent body 56 by a sailor (not illustrated) (second bonding process), and both end portions in the CD are overlapped and bonded by the third adhesive layer G3 formed by applying the hot melt adhesive M3 to an overlapping portion in advance, thereby forming a connecting portion 58$c$. For bonding of these portions, after the wrapping sheet 58 is folded back, the portions may be pressed and attached through a pair of pressure rolls 104. In this way, a continuous body of the absorbent element 50 to which the absorbent body 56 is intermittently fixed in the MD is formed in the barrel-shaped continuous body of the wrapping sheet 58 which is continuous in the MD.

In a case of manufacturing the underpants-type disposable diaper as in the present embodiment, the continuous body of the absorbent element 50 manufactured through the first bonding process and the second bonding process is interposed between the continuum-shaped top sheet 30 and the continuum-shaped liquid impervious sheet 11, and intermittently cut in the MD to become the individual inner members 200 after the continuous bodies of the leg gathers 60 are attached as necessary, and then attached to the continuous members of the separately manufactured outer members 12F and 12B, and folded in the front-back direction thereof to overlap each other. Thereafter, the side seal portions 12A are formed, and cutting is performed to obtain an individual diaper. When a pad type disposable diaper or a tape type disposable diaper is manufactured, the continuous body of the absorbent element is interposed between the continuum-shaped top sheet and the continuum-shaped liquid impervious sheet, and intermittently cut in the MD after the continuous bodies of the leg gathers are attached as necessary (fastening tapes are also attached in the case of the tape type disposable diaper), thereby becoming individual diapers.

When the connecting portion 58$c$ of the wrapping sheet 58 is located on the back face side of the absorbent body 56 as described above, after the absorbent element 50 is manufactured while maintaining an orientation immediately behind the fiber accumulating drum 102 as in the illustrated mode, a direction of the absorbent element 50 is reversed upside down by being reversed using rolls. Then, a member mounted on the front face side of the absorbent body 56 in the absorbent article may be attached to an upper side thereof, and a member mounted on the back face side of the absorbent body 56 in the absorbent article may be attached to a lower side thereof. Even when the direction of the absorbent element 50 is not reversed upside down, the member mounted on the back face side of the absorbent body 56 in the absorbent article may be attached to the upper side thereof, and the member mounted on the front face side of the absorbent body 56 in the absorbent article may be attached to the lower side thereof.

As illustrated in FIG. 14, in a preferable mode, the first adhesive layer G1 is formed on the wrapping sheet 58 to have a width larger than the sum of the width 56$x$ of the absorbent body 56 and both the thicknesses thereof 56$t$ in the first bonding process (a) to (b), and at least at the both end portions of the absorbent body 56 in the width direction, the folded portion and the upper surface of the absorbent body 56 are bonded through the first adhesive layer G1 applied to the folded portion and the second adhesive layer G2 applied to the upper surface of the absorbent body 56 in the second bonding process (c) to (d). In this way, on the lower surface side of the absorbent body 56 (the opposite side from the side having the connecting portion 58$c$ of the wrapping sheet 58), the internal surface of the wrapping sheet 58 is bonded to the absorbent body 56 only by the first adhesive. On the other hand, on the upper surface side of the absorbent body 56 (the side having the connecting portion 58$c$ of the wrapping sheet 58), at least in a region of the both end portions in the width direction, the internal surface of the wrapping sheet 58 is bonded to the absorbent body 56 by two layers corresponding to the first adhesive layer G1 and the second adhesive layer G2. As a result, on the upper surface side of the absorbent body 56 (the side having the connecting portion 58c of the wrapping sheet 58) where the adhesive force is likely to decrease rather than on the lower surface side of the absorbent body 56, the usage amount of the hot melt adhesives H1 and H2 at least in the region of the both end portions in the width direction may be increased more than that on the opposite side of the absorbent body 56. In addition, the side surface of the absorbent body 56 may be bonded without a gap. Therefore, it is possible to effectively suppress shape deformation of the absorbent body 56 while suppressing the total usage amount of the hot melt adhesives H1 and H2 for bonding the absorbent body 56 and the wrapping sheet 58 together.

Figure 17:
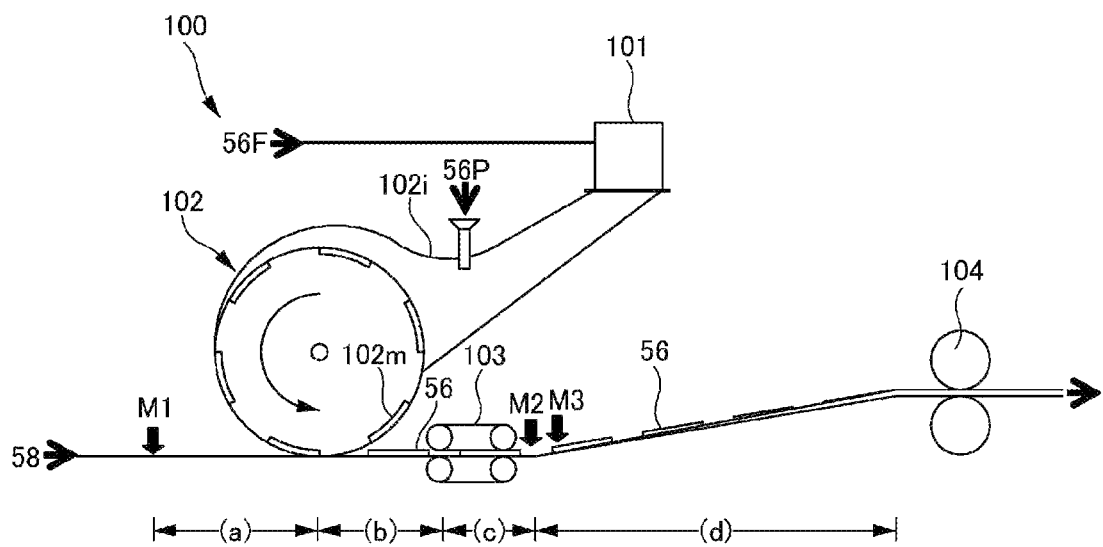
FIG. 17 is a schematic view illustrating a manufacturing facility for a conventional absorbent element.
Figure 18:
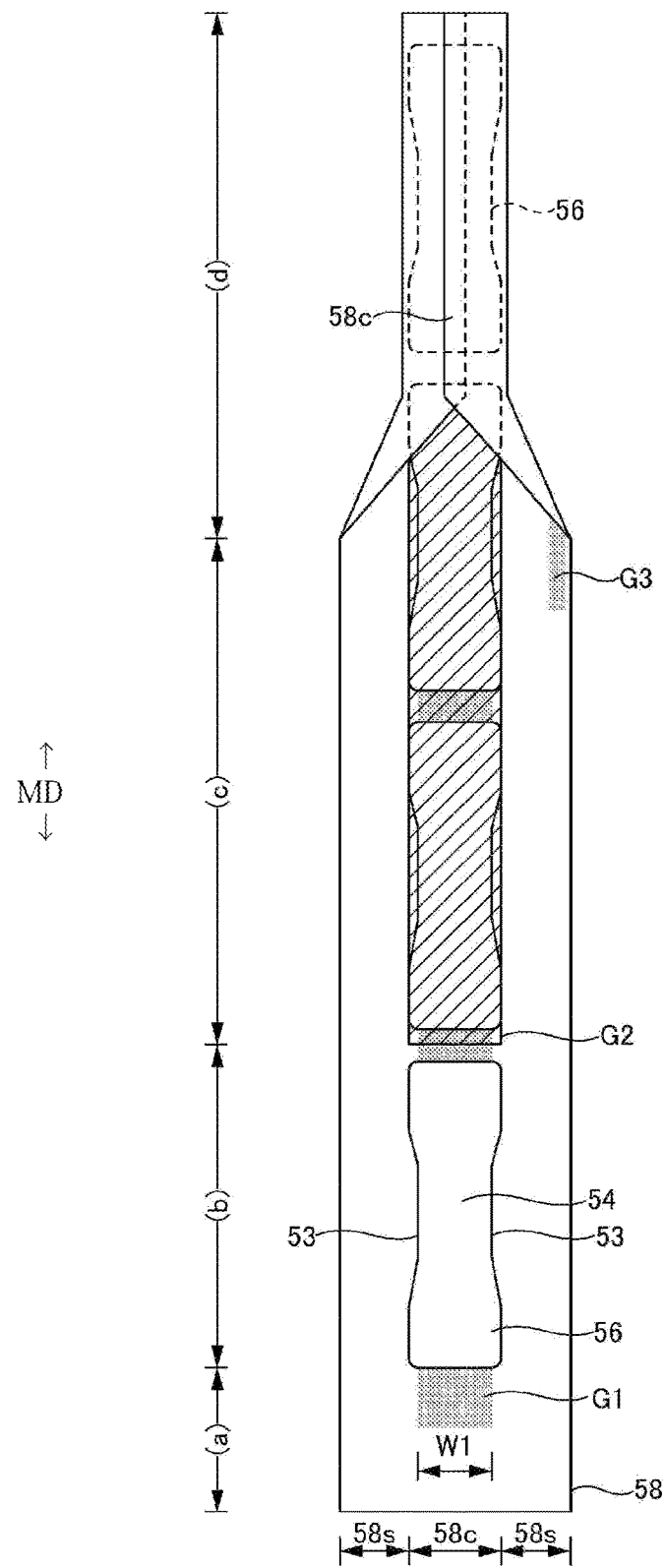
FIG. 18 is a plan view illustrating a manufacturing process of the conventional absorbent element.
Figure 19:
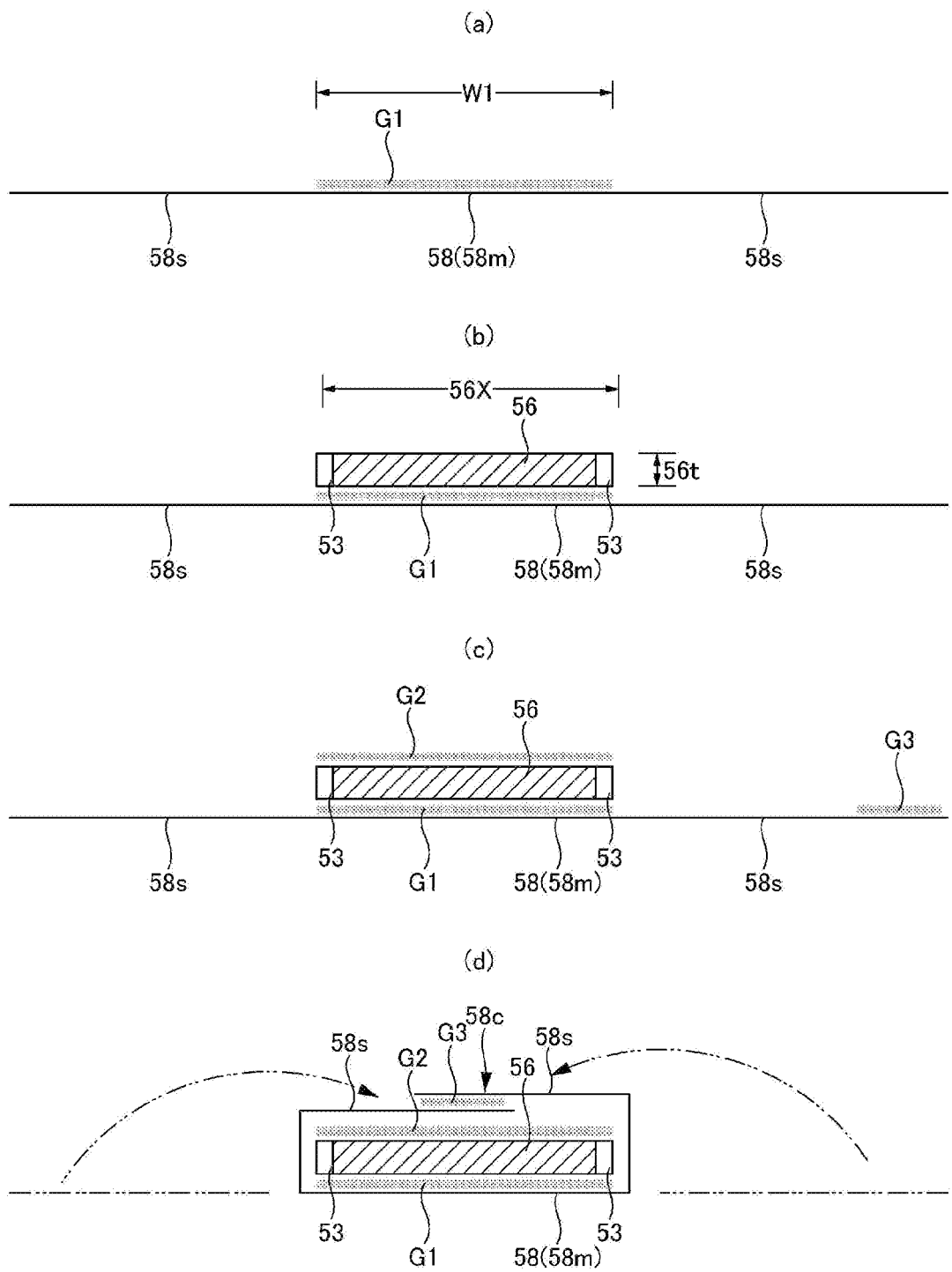
FIG. 19 is a cross-sectional view illustrating the manufacturing process of the conventional absorbent element.

In the case in which the first adhesive layer G1 is formed to have a width larger than the sum of the width of the absorbent body 56 and both the thicknesses of the absorbent body 56 as described above, when a press process is performed over the maximum width of the absorbent body 56 between the first bonding process (a) to (b) and the second bonding process (c) to (d) as illustrated in FIG. 17, there is concern that the first adhesive layer G1 protruding to the both sides of the absorbent body 56 in the width direction may adhere to a pressing device 103. Therefore, between the first bonding process (a) to (b) and the second bonding process (c) to (d), it is desirable that the press process of compressing the absorbent body 56 over the maximum width thereof is not performed or pressing is performed at a narrower width than the maximum width of the absorbent body 56 when the press process is performed. When the first adhesive layer G1 is formed to have a width smaller than the sum of the width of the absorbent body 56 and both the thicknesses of the absorbent body 56, the press process may be performed in the same manner as in a conventional example.

In the case in which the application width W1 of the first adhesive layer G1 is wider than the sum of the width 56x of the absorbent body 56 and both the thicknesses 56t of the absorbent body 56, when the narrowing portions 53 along the legs are included in the absorbent body 56 as in the illustrated mode, the width is preferably wider than a width obtained by further adding depression widths W2 of the narrowing portions 53 at the both sides in the CD. In this way, a part bonded by the two layers corresponding to the first adhesive layer G1 and the second adhesive layer G2 reaches an edge of each narrowing portion 53, and wrapping sheets 58 are strongly bonded by three layers corresponding to the first adhesive layer G1 on the connecting portion 58c side, the second adhesive layer G2, and the first adhesive layer G1 on the opposite side in a depressed part of the narrowing portion 53. Therefore, it is possible to effectively prevent shape deformation of the absorbent body 56 in the narrowing portions 53.

In addition, when the absorbent body 56 has the above-described slit 54 as in the mode illustrated in FIG. 12(b), the application width W1 of the first adhesive layer G1 is preferably wider than a width obtained by adding widths W3 each from a side edge of the absorbent body 56 to a side edge of the slit 54 to the both sides in the CD with respect to the sum of the width of the absorbent body 56 and both the thicknesses of the absorbent body 56. In this way, a part bonded by the two layers corresponding to the first adhesive layer G1 and the second adhesive layer G2 reaches an edge of the slit 54, and wrapping sheets 58 are strongly bonded by three layers corresponding to the first adhesive layer G1 on the connecting portion 58c side, the second adhesive layer G2, and the first adhesive layer G1 on the opposite side at least at the both end portions of the slit 54 in the width direction. Therefore, it is possible to effectively prevent shape deformation of the absorbent body 56 in the slit 54.

Further, as in the mode illustrated in FIG. 12(b), the application width W1 of the first adhesive layer G1 may be extended to an overlapping part of the wrapping sheet 58 to bond the overlapping part by the first adhesive layer G1.

An application pattern of the hot melt adhesives M1 and M2 for forming the first adhesive layer G1 and the second adhesive layer G2 is not particularly restricted. However, since the first adhesive layer G1 is applied in a wide range of the wrapping sheet 58 and serves as a base for adhesion between the wrapping sheet 58 and the absorbent body 56 (forming the above-described adhesive layer 561), permeability into the wrapping sheet 58 and the absorbent body 56 may not be increased. On the other hand, a main object of the second adhesive layer G2 is to increase shape maintainability of the absorbent body 56 by being impregnated into the absorbent body 56 (forming the above-described impregnation layer 562), and thus permeability into the absorbent body 56 is preferably high. From such a viewpoint, it is preferable that the hot melt adhesive M1 in the first adhesive layer G1 is applied in the form of a spiral or a mesh, and the hot melt adhesive M2 in the second adhesive layer G2 is applied in solid coating.

For the same reason, the hot melt adhesive M1 in the first adhesive layer G1 preferably has melt viscosity of 4,000 to 9,000 mPa·s, and the hot melt adhesive M2 in the second adhesive layer G2 preferably has melt viscosity of 1,000 to 6,000 mPa·s. In addition, it is preferable that the hot melt adhesive M2 in the second adhesive layer G2 has lower viscosity than the hot melt adhesive M1 in the first adhesive layer G1.

(Leg Gather)

The leg gathers 60 extend along both sides of the absorption surface of the inner member 200 in the width direction and rise toward the legs of the wearer, and are provided to block urine or loose stools moving in a lateral direction on the top sheet 30 and prevent side leak.

As illustrated in FIG. 3 and FIG. 4, each leg gather 60 of the present mode includes an inner nonwoven fabric layer 61 in an inner surface in the width direction, an outer nonwoven fabric layer 62 in an outer surface in the width direction, gather elastically stretchable members 63 provided along the front-back direction between the inner nonwoven fabric layer 61 and the outer nonwoven fabric layer 62 at least at tip portions in the middle in the front-back direction, and a liquid impervious sheet 64 (11) interposed between the inner nonwoven fabric layer 61 and the outer nonwoven fabric layer 62 over a range from a base to a position on a tip side of the base. In the illustrated mode, a part which has the liquid impervious sheet 64 in the leg gather 60 and is on the base side of the tip portion serves as a nonwoven fabric non-existing part 65 in which the inner nonwoven fabric layer 61 is not present and the liquid impervious sheet 64 is exposed across the whole leg gather 60 in the front-back direction. In this way, it is possible to reduce the usage amount of the nonwoven fabric by providing the nonwoven fabric non-existing part 65 in which the inner nonwoven fabric layer 61 is not present in the leg gather 60. In addition, since the tip portion of the leg gather 60 is a part coming into contact with the skin, when the nonwoven fabric non-existing part 65 is provided by avoiding the part, the liquid impervious sheet 64 rarely comes into contact with the skin, and deterioration of the touch may be suppressed.

In the mode illustrated in FIG. 1 to FIG. 6, the whole liquid impervious sheet 64 may be concealed by extending the inner nonwoven fabric layer 61 up to a side portion of the top sheet 30 or forming the leg gathers 60 having the structure illustrated in FIG. 7 and FIG. 8.

The gather elastically stretchable member 63 may be provided only at the tip portion of the leg gather 60. However, it is preferable that a plurality of gather elastically stretchable members is provided at an interval in a direction from the tip toward the base of the leg gather 60 as in the illustrated mode. In a normal case, the number of gather elastically stretchable members 63 is preferably two to six, and a mutual interval 60d therebetween is preferably 3 to 10 mm. In this way, when the plurality of gather elastically stretchable members 63 is provided at the interval, each interval part is depressed outward. Thus, when the nonwoven fabric non-existing part 65 is provided only in the interval part as in the illustrated mode, the liquid impervious sheet 64 exposed to the nonwoven fabric non-existing part 65 is rarely depressed to come into contact with the skin, and thus it is preferable. In this case, as in the mode illustrated in FIG. 1 to FIG. 6, it is particularly preferable to provide one or a plurality of gather elastically stretchable members 63 at an interval at least only in the tip portion and the base portion of the leg gather 60, respectively, and provide the nonwoven fabric non-existing part 65 only in an interval part between the gather elastically stretchable member 63 in the base portion and the gather elastically stretchable member 63 in the tip portion.

A front-back direction range in which the gather elastically stretchable member 63 is provided in the leg gather 60 may be set to the whole leg gather 60 in the front-back direction, and is preferably set to a front-back direction range of a rising part or less.

In addition, the gather elastically stretchable member 63 may be provided inside the liquid impervious sheet 64 incorporated in the leg gather 60 as in the mode illustrated in FIG. 3 and FIG. 9 or provided outside the liquid impervious sheet 64 as in the mode illustrated in FIG. 10 as long as the gather elastically stretchable member 63 is provided between the inner nonwoven fabric layer 61 and the outer nonwoven fabric layer 62 (for this reason, not provided in the nonwoven fabric non-existing part 65).

A range in which the liquid pervious film 64 is provided may be set to a range from the base to an intermediate position between the base and the tip as long as the range corresponds to a range from the base of the leg gather 60 to a position on the tip side of the base. However, the range is desirably provided up to the tip portion to sufficiently improve water-blocking capability, and is preferably set up to a position slightly spaced from the tip portion (for example, by the plurality of gather elastically stretchable members, specifically, about 5 to 30 mm) as in the mode illustrated in FIG. 3 and FIG. 4. Further, it is preferable to ensure flexibility of touch by not incorporating the liquid pervious film 64 in the tip portion.

In addition, in a mode in which the liquid impervious sheet 64 is exposed to the nonwoven fabric non-existing part 65, there is concern that the liquid impervious sheet 64 exposed to the nonwoven fabric non-existing part 65 may be pressed against the skin in a part 60W in which the front side outer member 12F and the back side outer member 12B overlap each other in the leg gather 60. However, when the part 60W is fixed to the front side outer member 12F and the back side outer member 12B and contracted in the width direction by the elastically stretchable members 15 and 19 of the front side outer member 12F and the back side outer member 12B as in the mode illustrated in FIG. 1 to FIG. 6, a contact area of the part 60W with respect to the skin remarkably decreases due to contraction wrinkles even when the liquid impervious sheet 64 is exposed. Thus, an influence on the touch is small. In the leg gather 60 of this mode, a region from the fixed portion 60W to the front side outer member 12F and the back side outer member 12B rises toward the leg as indicated by a two-dot chain line in FIG. 3 using the side edge of the absorbent body 56 as a base in response to contraction of the gather elastically stretchable member 63.

A member configuration of the leg gather 60 is not particularly restricted, and a known structure may be adopted. In the mode illustrated in FIG. 1 to FIG. 6, the top sheet 30 is made of a nonwoven fabric, both sides thereof in the width direction are configured to extend from the side edges of the absorbent body 56, a gather sheet 66 made of a nonwoven fabric is provided on the back face side of the absorbent body 56, both sides thereof in the width direction are configured to extend from the side edges of the absorbent body 56, each side end portion of the gather sheet 66 is folded back, a tip of a folded part 66r is spaced from the tip of the top sheet 30, and the liquid impervious sheet 64 is provided at least from between folded parts 66r of the gather sheet 66 to between the top sheet 30 and the gather sheet 66. Further, as a result, the outer nonwoven fabric layer 62 is formed by a part of the gather sheet 66 other than the folded part 66r, the inner nonwoven fabric layer 61 is formed by the folded part 66r of the gather sheet 66 and a part extending to a side of the absorbent body 56 in the top sheet 30, and the nonwoven fabric non-existing part 65 is formed by a part in which the folded part 66r of the gather sheet 66 is spaced from the top sheet 30. In this way, when the inner nonwoven fabric layer 61 on the base side of the nonwoven fabric non-existing part 65 in the leg gather 60 is formed by the top sheet 30, and the other part is formed by the gather sheet 66, the nonwoven fabric non-existing part 65 may be provided without cutting the material, a structure thereof is significantly simple, and manufacture is easy.

In this case, when the liquid impervious sheet 64 of the leg gather 60 is extended from one side of the leg gather 60 to the other side of the leg gather 60 through the back face side of the absorbent body 56 as in the mode illustrated in FIG. 3 and FIG. 4, it is possible to integrally ensure water-blocking capability of the back face side of the absorbent body 56 in addition to water-blocking capability of the leg gather 60, and thus it is preferable. However, as in the mode illustrated in FIG. 7 and FIG. 8, it is possible to individually provide the liquid pervious film 64 incorporated in the leg gather 60 and the liquid pervious film 11 covering the back face side of the absorbent body 56. In the latter case, a material of the liquid pervious film 64 incorporated in the leg gather 60 and a material 11 of the liquid pervious film covering the back face side of the absorbent body 56 may be identical to each other or different from each other.

Similarly, when the gather sheet 66 is formed by a single sheet from one leg gather 60 to the other leg gather 60 through the back face side of the absorbent body 56 as in the mode illustrated FIG. 3 and FIG. 4, a cloth-like external surface is obtained without separately providing the above-described crotch portion cover sheet, and thus it is preferable. However, the gather sheet 66 and a crotch portion cover sheet 12M may be separately provided as in the mode illustrated FIG. 7 and FIG. 8.

As another structure of the leg gather 60, it is possible to adopt a structure including a mounting part 68 fixed to the back face side of the inner member 200, an extended part 69 extended from the mounting part 68 to a side surface of the inner member 200 by being wrapped around a side of the inner member 200, a fallen down part 69B formed by both end portions of the extended part 69 in the front-back direction fixed to the side surface of the inner member 200 in a fallen down state, a free part 69F formed by not fixing an intermediate portion between the fallen down parts in the extended part, and the gather elastically stretchable member 63 fixed at least to a tip of the free part 69F along the front-back direction in a stretched state as in the mode illustrated FIG. 7 and FIG. 8. In this leg gather 60, in response to contraction of the gather elastically stretchable member 63, the free part 69F rises toward the leg indicated by a two-dot chain line in FIG. 9 using a boundary between the free part 69F and the mounting part 68 as the base.

The extended part 69 of the leg gather 60 of the mode illustrated FIG. 7 and FIG. 8 includes a root side part directed toward a center side in the width direction and a tip side part folded back outward in the width direction from a tip of the root side part. However, the extended part 69 may include only a part directed toward the center side in the width direction without being folded back outward in the width direction (not illustrated).

Meanwhile, in the intermediate region in the front-back direction corresponding to a rising part of the leg gather 60, at least one of a hot melt adhesive based on various application schemes and fixing means based on material welding such as heat sealing, ultrasonic sealing, etc. may be used for joining of the inner nonwoven fabric layer 61 and the outer nonwoven fabric layer 62 or fixing of the gather elastically stretchable member 63 interposed therebetween. It is preferred that the portions other than the bonded portions of the elastically stretchable gather members 63 not be bonded or be weakly bonded because bonding of the entire faces of the inner nonwoven fabric layer 61 and the outer nonwoven fabric layer 62 impairs flexibility. The illustrated mode has a structure in which fixing of the elongated elastically stretchable member to the inner nonwoven fabric layer 61 and the outer nonwoven fabric layer 62 and fixing between the inner nonwoven fabric layer 61 and the outer nonwoven fabric layer 62 are performed using only the hot melt adhesive applied to the outer peripheral surface of the gather elastically stretchable member 63 by applying the hot melt adhesive only to the outer peripheral surface of the gather elastically stretchable member 63 using application means such as comb gun or Surewrap nozzle, etc. and interposing the gather elastically stretchable member 63 between the inner nonwoven fabric layer 61 and the outer nonwoven fabric layer 62.

In addition, in a non-rising part at both sides of the leg gather 60 in the front-back direction, at least one of a hot melt adhesive based on various application schemes and fixing means 67 based on material welding such as heat sealing, ultrasonic sealing, etc. may be used for bonding of the inner nonwoven fabric layer 61 and the outer nonwoven fabric layer 62, fixing of the leg gather 60 having the mode illustrated in FIG. 1 to FIG. 6 to the front side outer member 12F and the back side outer member 12B, fixing of the root side part and the tip side part in the leg gather 60 having the mode illustrated in FIG. 7 and FIG. 8, and fixing thereof to the side surface of the inner member 200. In the illustrated mode, the hot melt adhesive and the fixing means 67 based on material welding are combined together. However, fixing may be performed using only one of the means.

Dimensions of the leg gather 60 may be appropriately determined. However, in a case of a disposable diaper for infants, a rising height of the leg gather 60 (an interval between the tip and the base in the width direction in the spread state) is preferably 15 to 60 mm, particularly 20 to 40 mm.

In each of the above modes, a material obtained by performing a water repellent treatment on a nonwoven fabric which is flexible and excellent in uniformity/concealing property such as spun bond nonwoven fabric (SS, SSS, etc.), SMS nonwoven fabric (SMS, SSMMS, etc.), melt blown nonwoven fabric, etc. using silicone, etc. as necessary may be suitably used as the inner nonwoven fabric layer 61 and the outer nonwoven fabric layer 62, and a fiber basis weight is preferably set to about 10 to 30 $g/m^2$. In the mode illustrated in FIG. 3 and FIG. 4, as understood from that fact that the inner nonwoven fabric layer 61 on the base side of the nonwoven fabric non-existing part 65 is formed by the top sheet 30, the materials of the inner nonwoven fabric layer 61 and the outer nonwoven fabric layer 62 may be made partially different from each other, and the materials of the inner nonwoven fabric layer 61 and the outer nonwoven fabric layer 62 may be made different from each other.

In each of the above modes, an elongated elastically stretchable member such as thread-like rubber, band-like rubber, etc. may be used as the gather elastically stretchable member 63. In a case of using a rubber thread, a fineness is preferably in a range of 470 to 1,240 dtex, more preferably in a range of 620 to 940 dtex. A stretch rate at the time of fixing is preferably in a range of 150 to 350%, more preferably in a range of 200 to 300%.

In each of the above modes, one row of leg gather 60 is provided on each of the left and right sides. However, a plurality of rows of leg gathers may be provided.

Description of Terms in Specification

When terms below are used in the specification, the terms have meanings below unless otherwise specified in the specification.

The "content rate of the high absorbent polymer particles" refers to a weight percentage.

The "front-back (longitudinal) direction" refers to a direction connecting a ventral side (front side) and a dorsal side (back side), and the "width direction" refers to a direction (left-right direction) orthogonal to the front-back direction.

The "spread state" refers to a flatly spread state without contraction or slack.

The "stretch rate" refers to a value when a natural length is set to 100%.

The "basis weight" is set as below. A sample or a specimen is pre-dried, and then is left in a test room or a device in a standard state (temperature 20±5° C., relative humidity 65% or less in a test location), and is put in a constant weight state. Pre-drying refers to setting the weight of the sample or the specimen to a constant weight in an environment in which relative humidity is in a range of 10 to 25% and temperature does not exceed 50° C. Pre-drying is unnecessary for a fiber having an official moisture regain of 0.0%. A sample having dimensions of 200 mm×250 mm (±2 mm) is cut off from the specimen in the constant weight state using a cutting template (200 mm×250 mm, ±2 mm). A weight of the sample is measured and multiplied by 20 to calculate a weight per square meter, and the weight is set to the basis weight.

A "thickness" is automatically measured using an automatic thickness measurement apparatus (KES-G5 handy Compression Tester) under the condition of a load of 10 gf/cm² and a pressurized area of 2 cm².

The "water absorption amount" is measured by JIS K7223-1996 "Testing method for water absorption capacity of super absorbent polymers".

The "water absorption rate" is set to a "time that elapses before the end point" when JIS K7224-1996 "Testing method for water absorption rate of super absorbent polymers" is performed using 2 g of high absorbent polymers and 50 g of physiological saline.

A "bending resistance" refers to JIS L 1096:2010 "8.21.1 Method A (45° cantilever method)" of a "Testing method for woven and knitted fabrics".

The "melt viscosity" is measured at a temperature of 140° C. using a Brookfield B type viscometer (Spindle No. 027) in accordance with JIS Z 8803.

The tests and measurements are carried out in a laboratory or an apparatus under normal conditions (a temperature of 20±5° C. and a relative humidity of 65% or less at the testing site), unless the environmental condition for the tests and measurements are otherwise specified.

The dimensions of the components are measured in a spread state, not a natural length state, unless otherwise specified.

INDUSTRIAL APPLICABILITY

The invention is suitable for an underpants-type disposable diaper as in the above example. However, the invention is applicable to a tape type or pad type disposable diaper and a general absorbent article such as a sanitary napkin.

REFERENCE SIGNS LIST

11 . . . liquid impervious sheet, 12F, 12B . . . outer member, 12A . . . side seal portion, 12B . . . back side outer member, 12F . . . front side outer member, 30 . . . top sheet, 40 . . . intermediate sheet, 50 . . . absorbent element, 56 . . . absorbent body, 58 . . . wrapping sheet, 60 . . . leg gather, 61 . . . inner nonwoven fabric layer, 62 . . . outer nonwoven fabric layer, 63 . . . gather elastically stretchable member, 64 . . . liquid impervious sheet, 65 . . . nonwoven fabric non-existing part, 66 . . . gather sheet, 66r . . . folded part, 200 . . . inner member, 12S . . . outer sheet layer, 12H . . . inner sheet layer, 19 . . . elastically stretchable member, 17 . . . waist portion elastically stretchable member, 15, 18 . . . under-waist portion elastically stretchable member, 16 . . . cover portion elastically stretchable member, 53 . . . narrowing portion, 54 . . . slit, 58c . . . connecting portion, H1, H2 . . . hot melt adhesive, 101 . . . defibrating machine, 102 . . . fiber accumulating drum, 100 . . . manufacturing facility, 102m . . . absorbent body mold, G1 . . . first adhesive layer, G2 . . . second adhesive layer, G3 . . . third adhesive layer, 56P . . . high absorbent polymer particles.

The invention claimed is:

1. An absorbent article, comprising
an absorbent element obtained by wrapping an absorbent body in a wrapping sheet,
wherein the absorbent body is obtained by mixing and accumulating fibers and high absorbent polymer particles, the absorbent body having a first face side and a second face side positioned opposite the first face side;
wherein the wrapping sheet includes an intermediate part and two side parts extending from the intermediate part in a width direction, wherein the intermediate part is located on the second face side of the absorbent body and both side parts are folded back to the first face side of the absorbent body from the intermediate part, and wherein distal ends of both side parts of the wrapping sheet are overlapped on the first face side of the absorbent body to form a connecting portion;
wherein a total weight of the high absorbent polymer particles is larger than a total weight of the fibers in the absorbent body;
wherein a content rate of the high absorbent polymer particles of the absorbent body increases stepwise or continuously from the first face side toward the second face side,
wherein a whole part of an internal surface of the wrapping sheet facing the absorbent body is bonded to an external surface of the absorbent body through a hot melt adhesive;
wherein a usage amount per area of the hot melt adhesive bonding the wrapping sheet and the absorbent body together is uniformly larger across a first region in its entirety than a second region, the first region comprising both side parts in the width direction on the first face side of the absorbent body and the second region is positioned on the second face side of the absorbent body;
wherein the absorbent body further comprises two narrowing portions formed by narrowing both sides of the absorbent body toward a center in the width direction at an intermediate portion in a front-back direction of the absorbent body; and
wherein the first region further comprises both narrowing portions in the width direction.

2. The absorbent article according to claim 1, wherein a slit penetrating the absorbent body in a thickness direction extends in the front-back direction at an intermediate portion of the absorbent body in the width direction, and
wherein the first region includes a whole part of the slit in the width direction.

3. The absorbent article according to claim 1, wherein in the first region, a number of stacked hot melt adhesive layers is larger than a number of stacked hot melt adhesive layers in the second region.

4. The absorbent article according to claim 1,
wherein a plurality of hot melt adhesive layers among which at least one of an application pattern and a type of the hot melt adhesive is different is stacked in the first region, and
a layer of the hot melt adhesive in the second region has the same application pattern and type as an application pattern and type of a layer located closest to the wrapping sheet among the plurality of hot melt adhesive layers in the first region.

5. A method of manufacturing an absorbent article using an absorbent element, comprising:
forming an absorbent body having a first face side and a second face side positioned opposite the first face side by accumulating a mixture of fibers and high absorbent polymer particles in at least one absorbent body mold while performing suction from a plurality of suction holes with a laterally disposed and rotationally driven fiber accumulating drum provided with, on an outer peripheral surface thereof, the absorbent body mold having a concave shape, a rotation direction corresponding to a front-back direction, and in a bottom face thereof, the plurality of suction holes;
transferring the absorbent body formed in the absorbent body mold to an intermediate part in a width direction on an upper surface of a wrapping sheet;

folding back side parts of the wrapping sheet located at both sides of the absorbent body in the width direction to the first face side of the absorbent body, respectively, overlapping distal ends of folded portions to form a connecting portion; and bonding a whole part of an internal surface of the wrapping sheet and an external surface of the absorbent body through a hot melt adhesive, thereby manufacturing the absorbent element obtained by wrapping the absorbent body in the wrapping sheet;

wherein a total weight of the high absorbent polymer particles is larger than a total weight of the fibers in the absorbent body;

wherein the accumulating is performed such that a content rate of the high absorbent polymer particles of the absorbent body formed in the absorbent body mold increases stepwise or continuously from a bottom side toward an inlet side of the absorbent body mold;

wherein a usage amount per area of the hot melt adhesive bonding the wrapping sheet and the absorbent body together is uniformly larger across a first region in its entirety than a second region, the first region comprising both side parts in the width direction on the first face side of the absorbent body and the second region is positioned on the second face side of the absorbent body;

wherein the absorbent body further comprises two narrowing portions formed by narrowing both sides of the absorbent body toward a center in the width direction at an intermediate portion in a front-back direction of the absorbent body; and wherein the first region further comprises both narrowing portions in the width direction.

6. The method of manufacturing an absorbent article according to claim 5, wherein after the absorbent body is transferred to the intermediate part in the width direction on the upper surface of the wrapping sheet, and before folding back the side parts of the wrapping sheet located at the both sides of the absorbent body in the width direction to the first face side of the absorbent body, respectively, a hot melt adhesive is applied to the first face side of the absorbent body.

7. The method of manufacturing an absorbent article according to claim 5, wherein after the manufactured absorbent element is reversed upside down, a member to be mounted on the second face side of the absorbent body in the absorbent article is attached to an upper side of the absorbent element, and a member to be mounted on the first face side of the absorbent body in the absorbent article is attached to a lower side of the absorbent element.

* * * * *